United States Patent
Jendralla et al.

(10) Patent No.: US 8,269,033 B2
(45) Date of Patent: Sep. 18, 2012

(54) PROCESS FOR CARBONYLATING PHENYLALKYL DERIVATIVES BY MEANS OF CARBON MONOXIDE

(75) Inventors: Joachim-Heiner Jendralla, Frankfurt (DE); Matthias Braun, Hochheim (DE); Gerhard Korb, Hainburg (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 467 days.

(21) Appl. No.: 12/508,798

(22) Filed: Jul. 24, 2009

(65) Prior Publication Data

US 2010/0069661 A1    Mar. 18, 2010

Related U.S. Application Data

(63) Continuation of application No. 11/612,971, filed on Dec. 19, 2006, now abandoned, which is a continuation of application No. PCT/EP2005/006414, filed on Jun. 15, 2005.

(30) Foreign Application Priority Data

Jun. 30, 2004  (DE) .......................... 10 2004 031 849

(51) Int. Cl.
C07C 67/36  (2006.01)
C07C 67/38  (2006.01)
C07C 51/10  (2006.01)
C07C 51/12  (2006.01)
C07C 51/14  (2006.01)

(52) U.S. Cl. ......................... 560/51; 562/406
(58) Field of Classification Search ........................ None
See application file for complete search history.

(56) References Cited

U.S. PATENT DOCUMENTS 2,634,294 A    4/1953   Butler

FOREIGN PATENT DOCUMENTS

| WO | WO95/00480 | 1/1995 |
|----|-----------|--------|
| WO | WO02/079134 | 10/2002 |
| WO | WO 03/000658 | 1/2003 |

OTHER PUBLICATIONS

Minisci et al., Solvent and Temperature Effects in the Free Radical Aerobic Oxidation of Alkyl and Acyl Aromatics Catalysed by Transition Metal Salts and N-Hydroxyphthalimide: New Processes for the Synthesis of p-Hydroxybenzoic Acid, Diphenols, and Dienes for Liquid Crystals and Cross-Linked Polymers, Organic Process Research & Development, vol. 8, No. 2, (2004), pp. 163-168.
Murray et al., Linear Free Energy Relationship Studies of the Dimethyldioxirane C-H Bond Insertion Reaction, J. Org. Chem. vol. 60 (1995), pp. 5673-5677.
Russell et al., The Photobromination of Branched-chain Hydrocarbons; the Dark Reaction of Bromine with Tertiary Alkyl Bromides, J. Amer. Chem. Soc. vol. 77, No. 15 (1995), pp. 4025-4030.
Truksa et al., Benzylic Hydrogen Atom Abstraction Utilizing Diethyl Bromomalonate as a Radical Source, J Org. Chem., vol. 57, No. 10, (1992) pp. 2967-2970.
Beilstein Abstract XP002208568, Database accession No. 937533.
Beilstein Abstract XP002353920, Database accession No. 1981278.

*Primary Examiner* — Yevegeny Valenrod
(74) *Attorney, Agent, or Firm* — Barbara E. Kurys, Esq.; Scully, Scott, Murphy & Presser, P.C.

(57) ABSTRACT

The invention is directed a process of preparing a compound of formula (I),

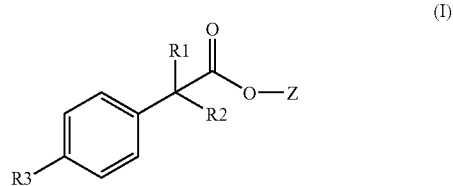

wherein R1, R2, R3 and z are as defined herein.

5 Claims, No Drawings

PROCESS FOR CARBONYLATING PHENYLALKYL DERIVATIVES BY MEANS OF CARBON MONOXIDE

This application is a Continuation of International Application No. PCT/EP2005/006414, filed Jun. 15, 2005.

FIELD OF THE INVENTION

The invention relates to a process for preparing phenylalkylcarboxylic acid derivatives of the formula I with carbon monoxide in the presence of super-acids. The invention further relates to halo-[4-(1-hydroxy-1-methylethyl)-phenyl]alkyl-1-one derivatives of the formula X.

BACKGROUND OF THE INVENTION

The process products are sought-after compounds for the preparation of a multitude of subsequent products, for example for the preparation of anti-allergic medicaments such as 4-[4-[4-(hydroxydiphenylmethyl)-1-piperidinyl]-1-hydroxybutyl]-alpha,alpha-dimethylphenylacetic acid, referred to below as fexofenadine (U.S. Pat. No. 4,254,129). The central synthetic building block in the preparation of fexofenadine is 2-[4-(4-chlorobutanoyl)phenyl]-2-methyl-propionic acid.

Known processes for preparing 2-[4-(4-chlorobutanoyl) phenyl]-2-methyl-propionic acid (EP0703902, WO95/00482, U.S. Pat. No. 4,254,129, WO97/23213, WO97/22344, WO95/00480, WO93/21156, U.S. Pat. No. 4,254,130, WO2003/000658) have a high number of stages and lead to p and m positional isomers which subsequently have to be separated from one another. In addition, the intermediates in the known processes often have to be purified by column chromatography, which complicates the synthesis of large amounts of substance in a pilot plant or on the production scale.

It has now been found that the disadvantages mentioned can be avoided by a short, efficient and isomer-free synthesis which also dispenses with costly and inconvenient purification steps such as column chromatography.

The object is achieved by carbonylating the compounds of the formula II with carbon monoxide in the presence of a superacid. In this way, the formation of positional isomers is prevented and the compounds of the formula (I) can be prepared in only 2 to 4 synthetic stages with high yield and purity.

SUMMARY OF THE INVENTION

The invention therefore relates to a process for obtaining the compound of the formula I

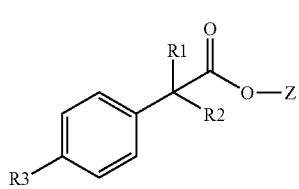

and/or a salt of the compound of the formula I where
R1 and R2 are the same or different and are each independently —$(C_1$-$C_4)$— alkyl,
R3 is
 1) —C(O)—$(C_1$-$C_4)$-alkyl in which alkyl is unsubstituted or monosubstituted by Cl or Br, or
 2) —C(O)—$(C_3$-$C_6)$-cycloalkyl, and
Z is a hydrogen atom or —$(CH_2)_n$—$CH_3$ where n is the integer zero, 1, 2, 3, 4, 5, 6, 7, 8 or 9, which comprises reacting a compound of the formula II

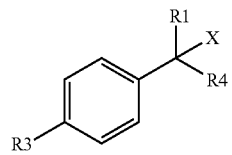

where
R1 and R3 are each as defined in formula I,
X is Cl, Br or —OH and
R4 is as defined for the R2 radical in formula I or, together with X, is a C=C double bond
with carbon monoxide and/or a carbon monoxide-releasing compound in the presence of concentrated sulfuric acid ($H_2SO_4$), hydrogen fluoride (HF) and/or of a superacid, and then
a) adding water in order to obtain the compound of the formula I in which Z is a hydrogen atom or
b) adding $(C_1$-$C_{10})$-alkyl-OH when X is Cl or Br, or R4, together with X, is a C=C double bond, in order to obtain the compound of the formula I in which Z is —$(C_1$-$C_{10})$-alkyl.

DETAILED DESCRIPTION OF THE INVENTION

The invention also relates to a process for obtaining the compound of the formula I where
R1 and R2 are simultaneously methyl,
R3 is
 1. —C(O)-propyl where propyl is monosubstituted by Cl or
 2. —C(O)-cyclopropyl and
Z is a hydrogen atom or —$(CH_2)_n$—$CH_3$ where n is the integer zero, 1, 2 or 3.

In process step b), preference is given to adding methanol, ethanol, 1-propanol or 1-butanol in order to obtain the compound of the formula I in which Z is —$(CH_2)_n$—$CH_3$ and in which n is the integer zero, 1, 2 or 3.

The invention also relates to a process for obtaining the compound of the formula I, wherein the reaction is carried out in the presence of solvents which are sufficiently inert toward superacids.

The invention also relates to a process for obtaining the compound of the formula I in which Z is a hydrogen atom, wherein a compound of the formula I in which Z is —$(C_1$-$C_{10})$-alkyl is cleaved to the corresponding alcohol and carboxylic acid.

The invention also relates to a process for obtaining the compound of the formula I, wherein the reaction is carried out in the presence of an additive which is converted to metal carbonyls in the presence of carbon monoxide.

The term "$(C_1$-$C_4)$-alkyl" refers to hydrocarbon radicals whose carbon chain is straight or branched and contain from 1 to 4 carbon atoms, i.e. methyl, ethyl, propyl, isopropyl, butyl, isobutyl, sec-butyl or tert-butyl.

The term "—$(CH_2)_n$—$CH_3$ where n is the integer zero, 1, 2, 3, 4, 5, 6, 7, 8 or 9" or "—$(C_1$-$C_{10})$-alkyl" refers to hydrocarbon radicals whose carbon chain is straight or branched and contains from 1 to 10 carbon atoms, for example methyl, ethyl, n-propyl, isopropyl, n-butyl, isobutyl, pentyl, hexyl, heptyl, octyl, nonyl or decyl.

In the case that n is zero in the "—$(CH_2)_n$—$CH_3$" radical, the result is a methyl radical.

The term "$(C_1$-$C_{10}$-alkyl-OH)" refers to alcohols such as methanol, ethanol, 1-propanol, isopropanol, 1-butanol, isobutanol, sec-butanol, pentanol, hexanol, heptanol, octanol, nonanol or decanol.

$(C_3$-$C_6)$-cycloalkyl radicals are, for example, compounds which derive from 3- to 6-membered monocycles such as cyclopropyl, cyclobutyl, cyclopentyl or cyclohexyl.

The term "carbon monoxide-releasing compound" refers to compounds which release carbon monoxide (CO) under reaction conditions, for example formic acid, formate salts with inorganic or organic cations, and metal carbonyls.

The term "superacids" refers to acids which have a higher acidity than concentrated sulfuric acid ($H_O$=−12). Examples of superacids are protic acids such as perchloric acid, chlorosulfonic acid, fluorosulfonic acid, trifluoromethanesulfonic acid, perfluorobutane-1-sulfonic acid, Lewis acids such as $SO_3$, aluminum trichloride or antimony pentafluoride, or conjugated protic acid-Lewis acid complexes, for example sulfuric acid with $SO_3$ (oleum; polysulfuric acids), sulfuric acid with boric acid [$HB(HSO_4)_4$], fluorosulfonic acid with antimony pentafluoride (magic acid), trifluoromethanesulfonic acid with antimony pentafluoride, hydrogen fluoride with antimony pentafluoride ($HSbF_6$), HF with $TaF_3$, $BF_3$ with HF ($HBF_4$, tetrafluoroboric acid), $H_3PO_4$ with $BF_3$, or fluorosulfonic acid with $SO_3$, or conjugated complexes of, for example, $HSO_3F$ with HF and $SbF_5$, or $HSO_3F$ with $SO_3$ and $SbF_5$. Such superacids are described, for example, in G. A. Olah, G. K. Surya Prakash, "Superacids", John Wiley & Sons, New York, 1985, pages 33-51. The definition of the superacids is described in G. A. Olah, G. K. Surya Prakash, "Superacids", John Wiley & Sons, New York, 1985, pages 4 to 7; the definition of the term superacid which has been adopted here is found there on page 7, the definition of acid strength $H_O$ on page 4.

The inert solvents used may, for example, be liquid sulfur dioxide, super-critical carbon dioxide, sulfolane and n-alkanes having from 4 to 12 carbon atoms. For some of the superacids, it is also possible to use chlorobenzene, fluorobenzene, toluene, cumene, halogenated hydro-carbons, methyl acetate, ethyl acetate, n-butyl acetate and other solvents.

The term "additive" refers primarily to compounds which, under contact with carbon monoxide, are converted rapidly to metal carbonyls, and are firstly readily soluble and secondly dissociate readily in concentrated sulfuric acid or superacids. Examples of these compounds are copper(I) oxide, silver(I) oxide and silver nitrate. Useful additives are also inexpensive metal carbonyls which can transfer CO ligands to carbocations, preferably with subsequent reformation of the starting metal carbonyl by reaction with CO. Examples of such metal carbonyls are iron pentacarbonyl $Fe(CO)_5$, disodium tetracarbonylferrate(-2) $Na_2Fe(CO)_4$, octacarbonyldicobalt(0) $Co_2(CO)_8$ and nickel tetracarbonyl $Ni(CO)_4$.

The term "cyclopropyl keto derivative of formula III" refers to the following compound:

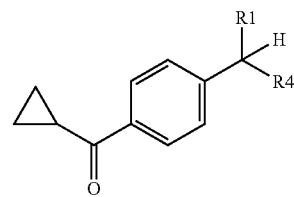

The acids mentioned enable the carbonylation of the reactant of the formula (II) by generating carbocations of the formula (A) by protonation of the X group followed by HX elimination (or, in the case of the alkene in which X and R4 together are an α,β-C═C double bond, by protonation of this double bond). These carbocations react with carbon monoxide to form acylium ions of the formula (B) from which the carboxylic acid of the formula (I) is formed by reaction with water or the corresponding esters of the carboxylic acid (I) are formed by reaction with a $C_1$-$C_{10}$-alcohol.

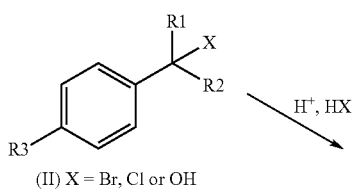

(II) X = Br, Cl or OH

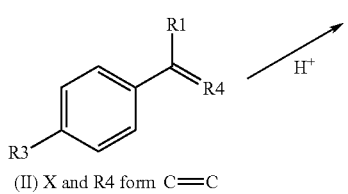

(II) X and R4 form C═C

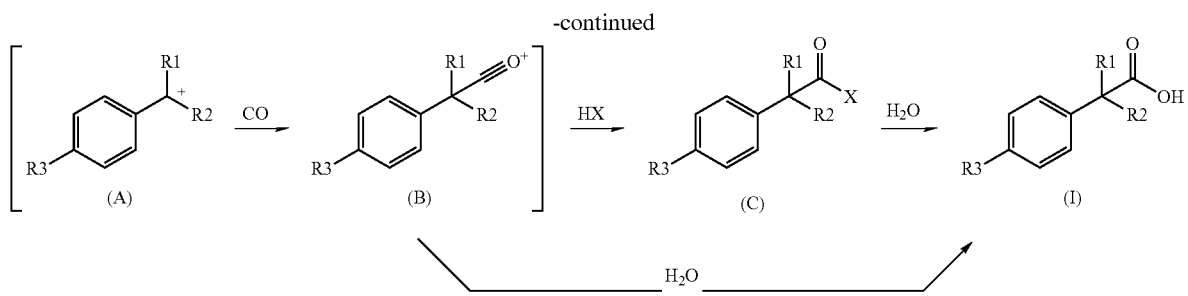

The synthesis of carboxylic acids by carbonylating corresponding alcohols, halides or alkenes with carbon monoxide in the presence of strong acids is known in principle. Reviews of such reactions can be found in:

H. Bahrmann in "New Syntheses with Carbon Monoxide", E. Falbe Edit., Springer Verlag New York 1980, ch. 5 "Koch Reactions", page 372-413;

Houben-Weyl "Methoden der Organischen Chemie" [Methods of Organic Chemistry] Georg Thieme Verlag Stuttgart 1985, Volume E5 (carboxylic acids and carboxylic acid derivatives), page 315-322;

A. L. Lapidus, S. D. Pirozhkov "Catalytic synthesis of organic compounds by the carboxylation of unsaturated hydrocarbons and alcohols", Russian Chemical Reviews 1989, 58(2), page 117-137;

"Encyclopedia of Reagents for Organic Synthesis", L. A. Paquette Edit., John Wiley New York 1995, Vol. 2, Carbon Monoxide, Reactions with Carbocations, page 991.

However, this reaction had not yet been used to synthesize carboxylic acids of the formula (I) from reactants of the formula (II) via α,α-dialkylbenzylcarbenium ions of the formula (A). In general, it has to date not been possible to prepare α,α-dialkylarylacetic acids by carbonylation, neither by cationic carbonylation nor by free-radical or transition metal-catalyzed carbonylation.

The reaction may be carried out in such a way that the strong acid functions simultaneously as a promoter and as a solvent. In this embodiment, preference is given to those acids which can be recovered cheaply or simply and which have a high dissolution capacity for carbon monoxide. Particularly cheap acids are, for example, sulfuric acid, oleum, sulfuric acid-boric acid, $BF_3$—$H_3PO_4$ complex and HF—$BF_3$, the first three being advantageous from the environmental standpoint. Although trifluoro-methanesulfonic acid or perfluorobutane-1-sulfonic acid are relatively expensive, they can be recovered virtually quantitatively in a simple manner from aqueous workup residues and have substantially higher dissolution capacity for carbon monoxide. According to B. L. Booth et al., J. Chem. Soc. Perkin Trans. I, 1979, page 2443, 155 ml of CO per liter of 95% trifluoromethanesulfonic acid dissolve at 27° C. and standard pressure, while only 21 ml of CO per liter of 95% sulfuric acid dissolve under the same conditions. The higher CO concentration in $CF_3SO_3H$ by a factor of 7 leads to higher carbonylation rates of the carbocation (A) and brings about, together with the higher acid strength ($H_O$ about −14 for $CF_3SO_3H$, $H_O$ about −12 for concentrated $H_2SO_4$), improved yields of the carboxylic acid (I).

Alternatively, the reaction may also be carried out in a solvent which is preferably inert toward the strong acids mentioned, in which case the strong acid is used only as a promoter. The inert solvents used may, for example, be liquid sulfur dioxide, supercritical carbon dioxide, sulfolane and n-alkanes; for some of the superacids, it is also possible, for example, to use chlorobenzene, fluorobenzene, toluene, cumene, halogenated hydro-carbons, methyl acetate, ethyl acetate, n-butyl acetate and other solvents. Alternatively, the reaction may also be carried out without solvent in the case of liquid reactants (II), and in suspension in the case of solid reactants (II). In the case of liquid reactants (II), this is the preferred embodiment.

In a further embodiment, the carbonylation reaction is carried out in an autoclave whose stirrer preferably ensures an efficient introduction of the gas phase (carbon monoxide) into the liquid phase, for example a sparging stirrer. In addition, this autoclave is equipped with a device which permits metering against CO pressure. The acid and optionally an additive, optionally dissolved in a preferably inert solvent, are initially charged in the autoclave. The air in the autoclave is displaced by nitrogen with stirring, and then carbon monoxide is injected with the desired pressure. Subsequently, at the desired reaction temperature, the reactant (II), optionally dissolved in acid-inert solvent, is added slowly. The mixture is stirred further until the intermediate (B) or (C) has achieved its maximum, and then the reaction mixture, optionally after preceding decompression of the gas phase, is forced into a second reactor in which either an excess of water or an excess of $C_1$- to $C_{10}$-alcohol has been initially charged close to 0° C. with cooling. Alternatively, quench/workup of the reaction mixture, at least after use of a portion of the superacids mentioned, can also be carried out by directly metering in an excess of water or an excess of $C_1$- to $C_{10}$-alcohol, with cooling, into the reaction autoclave. This workup method is unsuitable for the superacids, whose reaction with water or the alcohols mentioned is too strongly exothermic. The additives mentioned are compounds which are converted under contact with CO rapidly to metal carbonyls which are firstly readily soluble and secondly dissociate readily in concentrated sulfuric acid or superacids. In this way, such additives increase the availability of CO in the liquid phase. A preferred additive is, for example, copper(I) oxide ($Cu_2O$). It is converted in <80% sulfuric acid on contact with CO to copper (I)-monocarbonyl ion $Cu(CO)^+$. However, in >80% sulfuric acid and in superacids, further addition of CO proceeds to form the copper(I)-tricarbonyl ion $Cu(CO)_3+$, the equilibrium being shifted in favour of $Cu(CO)_3+$ by increased CO pressure, reduced temperature and increased acid strength. In 100% sulfuric acid, for example at −10° C., 2.2 CO ligands are present per Cu+ ion under 1 atm of CO, 3.0 CO ligands per Cu+ ion under 7 atm of CO [see Y. Souma, H. Sano, J. Iyoda J. Org. Chem. 1973, 38, 2016-2020]. In the presence of CO acceptors such as carbo-cations (A), CO is transferred from the $Cu(CO)_3+$ ion, with reformation of $Cu(CO)+$, to the carbocations to form acylium ions (B). The Cu+ acts as a "CO carrier" from the gas phase to the reacting carbocations in the solution. The slow metering of the reactant (II) to the initially charged solution of CO in strong acid (plus optionally inert solvent) serves to minimize the steady-state concentration of carbocations (A). When the concentration of the carbocations (A) is too high, the reaction of (A) with CO to give the acylium ion (B) proceeds relatively slowly and the superacid used is not strong enough to suppress all proton eliminations, a portion of the carbocations (A) can be converted by proton elimination from the α-position to the alkene of the formula (II) (X and R4 together are a C=C double bond) which can then react with remaining carbocations (A) in the form of a cationic polymerization to form oligomers and polymeric products. The metered addition of the reactant, the use of suitable additives and the use of stirrers with particularly effective gas introduction into the liquid phase bring about significant yield improvements of the desired carboxylic acid (I) when:

the promoter acid used has only poor to moderate dissolution capacity for CO, the acid strength of the promoter acid is at the lower end of the acid strength needed for carbocation generation, the carbonylation is carried out at particularly low CO pressure.

When particularly suitable promoter acids having a high CO dissolution capacity and high acid strength $H_O$, for example trifluoromethanesulfonic acid, are used, it is possible at CO pressures from about 20 bar to dispense with the metered addition of the reactant, the use of additives and special stirrers without yield reduction. This leads to the following two procedures which are technically particularly simple to carry out:

A) The superacid, concentrated sulfuric acid or hydrogen fluoride, optionally dissolved in an inert solvent, are initially charged in an autoclave. The air in the autoclave is displaced by nitrogen with stirring and then carbon monoxide is injected. The mixture is left to stir for about 30 minutes, so that the liquid phase becomes saturated with CO. The gas phase is then decompressed, the entire amount of the reactant (II) is added at once with exclusion of air and CO is immediately injected again up to the desired pressure. Quench/workup are effected as described above.

B) A reactor is initially charged with the reactant (II), optionally dissolved in an inert solvent. In a second reactor, the dissolved air is displaced from the superacid and the superacid is optionally saturated with carbon monoxide (CO). The superacid is then forced all at once into the reactor comprising the initially charged reactant and CO is subsequently immediately injected to the desired pressure. Quench/workup are effected as described above.

The carbonylations are effected at a CO pressure of from 1 bar to 500 bar, preferably from 1 to 40 bar, more preferably from 5 to 25 bar.

The reaction temperature in the carbonylation is from −70° C. to +100° C., preferably from −10° C. to +50° C., more preferably from 0° C. to +40° C.

The reaction time is generally in the range from 5 minutes to 2 days, preferably from 15 minutes to 5 hours, depending on the composition of the reaction mixture, selected temperature range and CO pressure.

When the superacid functions simultaneously as a promoter of the carbonylation reaction and as a solvent, from 0.1 mol to 5.0 mol of the reactant (II) are used per liter of superacid, preferably from 0.3 mol to 3.0 mol, more preferably from 0.4 mol to 2.0 mol. When the superacid functions only as a promoter, i.e. the reaction is carried out either without solvent or using a preferably acid-inert solvent, less superacid is required. Preferred superacids are oleum, sulfuric acid with boric acid, HF with $BF_3$, $BF_3.H_3PO_4$ complex, aluminum trichloride, chlorosulfonic acid, fluoro-sulfonic acid, trifluoromethanesulfonic acid or perfluorobutane-1-sulfonic acid, in particular trifluoromethanesulfonic acid.

Additives ("CO carriers") are used in an amount of from 5 mol % to 100 mol % based on the reactant (II), preferably from 10 to 30 mol %, in particular about 20 mol %.

The invention also relates to a process, wherein the compound of the formula II is reacted with carbon monoxide or a carbon monoxide-releasing compound in the presence of water, water being used in an amount of from 2 mol % to 800 mol % based on the compound of the formula II, and of concentrated sulfuric acid or hydrogen fluoride or of a superacid or mixtures thereof.

In the case of the carbonylation of the bromide of the formula (II) [X=bromo, R1=R2=methyl, R3=4-chlorobutyryl] in trifluoromethanesulfonic acid, the completeness of the conversion of the reactant (II), and the achieved yield and purity of the desired carboxylic acid (I) depend upon the water content of the trifluoromethanesulfonic acid. It is advantageous to add water to the reaction mixture. Water is added in an amount of from 50 mol % to 500 mol % based on the reactant (II), preferably from 90 to 300 mol %, in particular about 200 mol %.

The water can be introduced into the autoclave by different procedures. The water may be present in the autoclave from the start. The calculated amount of water may be added, for example, to the trifluoromethane-sulfonic acid. The reaction may then be carried out as shown above.

In the case of larger batches, it may be advantageous not to add the amount of water required until during the carbonylation as it proceeds. In this case, the autoclave is charged first with the dry trifluoromethane-sulfonic acid. After the inertization, establishment of the reaction temperature and injection of the reactant solution, a calculated amount of water-containing trifluoromethanesulfonic acid, for example trifluoromethanesulfonic acid monohydrate, may then be metered in. 100 mol % of water is consumed by the conversion of the acylium ion (B) to the carboxylic acid (I) in the carbonylation mixture.

The direct addition of water into the carbonylation solution is very exothermic and is therefore to be avoided if at all possible.

The carboxylic acid of the formula (I), or the methyl or ethyl ester thereof, from the carbonylation solution admixed with an excess of water, or an excess of the alcohol mentioned, is isolated with methods which are known to those skilled in the art. The optimal isolation method depends upon the presence or absence of organic solvents, the nature of the substituents R1, R2 and R3, and the nature of the superacid used and, where present, of the additive.

Principles of the isolation are:

in the absence of organic solvents, direct crystallization of the carboxylic acid (I) from the aqueous solution, supported by cooling and seeding with authentic carboxylic acid.

extraction of the acidic aqueous mixture with a suitable water-immiscible organic solvent, for example toluene, ethyl acetate, MTB ether or dichloromethane, followed by washing of the organic extracts with water to remove residues of promoter acid, followed by filtration of the organic phase and evaporation of the solvent, for example under reduced pressure.

The isolation of the carboxylic acid (I) [R1=R2=methyl, R3=4-chloro-butyryl] from the carbonylation reactions in trifluoromethanesulfonic acid is described in the examples.

Advantages of the process according to the invention are, for example when trifluoromethanesulfonic acid is used, a clean and quantitative reaction. The purity even of the crude carboxylic acids (compound of the formula I) was, according to HPLC analyses, from more than 95 to 99 area percent, which was also confirmed by $^1$H NMR spectra of the crude, isolated carboxylic acids.

The handling of aggressive liquid superacids (particularly on a large scale), the workup of the products from the carbonylation reaction and the recovery of the superacid can be simplified when the latter is used in immobilized form on a solid support. The preparation of solid polytrifluoromethanesulfosiloxane superacid on supports such as silica gel, alumina or bentonites has already been described in the prior art. These immobilized catalysts have been used successfully for Friedel-Crafts acylations of benzene derivatives and alkylations of branched hydrocarbons (mild reaction conditions, up to 98% yield, repeated reuse without loss of activity, no "bleeding" of trifluoromethanesulfonic acid into the reaction solution):

R.-J. Hu, B.-G. Li Catalysis Letters 2004, 98 (1), 43-47;
D.-Q, Zhou, Y.-H. Zhang, M.-Y. Huang, Y.-Y. Jiang Polymers for Advanced Technologies 2003, 14 (3-5), 360-363;
F. Boisson, L. Gambut, G. Mignani (Rhodia Chimie) WO 2003080710 A1
D.-Q. Zhou, C.-M. Wang, J.-H. Yang, M.-Y. Huang, Y.-Y. Jiang Polymers for Advanced Technologies 2002, 13 (3-4), 169-172;
A. de Angelis, C. Flego, P. Ingallina, L. Montanari, M. G. Clerici, C. Carati, C. Perego Catalysis Today 2001, 65 (2-4), 363-371;
D.-Q. Zhou, J.-H. Yang, G.-M. Dong, M.-Y. Huang, Y.-Y. Jiang Journal of Molecular Catalysis A: Chemical 2000, 159 (1), 85-87;
F. J.-Y. Chen, C. Le Deore, T. Hamaide, A. M. Guyot, V. Pinjala, J. D.-Y. Ou, U.S. Pat. No. 6,060,633 A (2000);
R. L. Mehlberg, G. A. Huff, Jr. (Amoco Corp., USA) WO 9852887 A1 (1998).

The invention therefore also relates to the use of immobilized trifluoro-methanesulfonic acid or immobilized fluorosulfonic acid for the carbonylation of reactants of the formula (II) to products of the formula (I). Suitable supports for trifluoromethanesulfonic acid ($CF_3SO_3H$) or fluoro-sulfonic acid ($FSO_3H$) are solids which are inorganic oxides which have free hydroxyl groups on their surface. They may be simple oxides such as silicon oxide (silica gel, silica), aluminum oxide (alumina), titanium oxide (titania) or magnesium oxide (magnesia), but may also be multiple and complex oxides such as silica-alumina, silica-alumina-thoria, zeolites or clay earths (clays). Examples of such inorganic oxides include silica, alumina, titania, magnesia, silica-alumina, silica-titania, silica-magnesia, silica-alumina-thoria, silica-alumina-zirconia, crystalline aluminosilicates, including synthetic zeolites such as A-, X- and ZSM-5 zeolites, naturally occurring zeolites such as faujasite and mordenite, and also clay earths such as bentonite and montmorillonite.

Trifluoromethanesulfonic acid or fluorosulfonic acid may be bound either chemically to the solid support or only physically strongly adsorbed on the support surface.

The chemical binding to the solid support may be effected by different methods. For example, trifluoromethanesulfonic acid can be immobilized by formation of polytrifluoromethanesiloxanes on the support surface, as described by:
a) R.-J. Hu, B.-G Li, Catalysis Letters 2004, 98 (1), 43-47
b) D.-Q. Zhou, Y.-H. Zhang, M.-Y. Huang, Y.-Y. Jiang, Polymers for Advanced Technologies 2003, 14 (3-5), 360-363
c) D.-Q. Zhou, J.-H. Yang, G.-M. Dong, M.-Y. Huang, Y.-Y, Jiang, Journal of Molecular Catalysis A: Chemical 2000, 159, 85-87

In this method, the solid support, preferably a silicon oxide of very low density and large surface area (known as "fumed silica") or alumina is boiled under reflux with ethyl orthosilicate, water, $CF_3SO_3H$ and ethanol, the solvent is distilled off and the solid residue is heated to about 180° C. The principle of this chemical bonding is outlined in the following scheme:

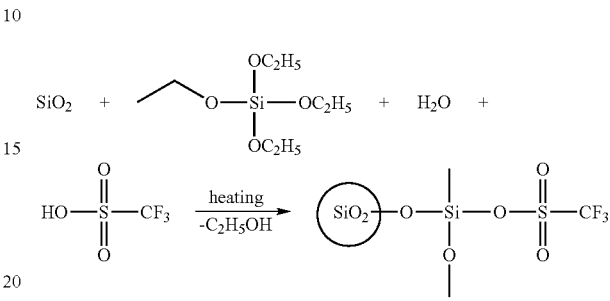

Alternatively, the chemical binding of the superacid may also be effected by reacting the solid support dehydrated by heating under reduced pressure in an inert solvent with an alkyl metal halide $X_nMR_m$ and reacting the resulting product with the superacid. In this formula, X is a halide, M is a metal, preferably aluminum, boron, tin or magnesium, and R is a monovalent hydrocarbon radical. n and m are integers which correspond to the valence requirements of M. Both n and m may be zero. In the first case, the compound is an alkyl-metal compound, in the latter case a metal halide. Preferred definitions of $X_nMR_m$ are $AlCl_3$, $C_2H_5AlCl_2$, $(C_2H_5)_2AlCl$, $(C_2H_5)_3Al$, $BCl_3$, $SnCl_4$ and $MgBu_2$ where Bu is a butyl radical.

This method has been described by:
d) F. J. Chen, C. LeDeore, T. Hamaide, A. M. Guyot, V. Pinjala, J. D.-Y. Ou, U.S. Pat. No. 6,060,633 (2000)

The principle of this chemical binding is outlined by way of example in the following scheme:

Silica gel (approx. 300 m$^2$/g) — Dehydrating 450° C./under reduced pressure/1 h →

```
  |              |
  Si — O — Al-iBu
  |              |    CF_3SO_3H
                iBu   ─────────→
                      in heptane
  Si — O — Al-iBu    25° C., 1 h
  |              |
                iBu
```

1M Al(iBu)$_3$ in heptane, 25° C., 1 h →

```
  |              |
  Si — O — Al — O_3SCF_3
  |              |
                O_3SCF_3
  Si — O — Al — O_3SCF_3
  |              |
                O_3SCF_3
```

Drying at 100° C. under reduced pressure iBu represents the isobutyl radical

Alternatively, the superacid may also be heated with the solid support, preferably silica gel 60, with exclusion of moisture, just below the boiling point (to 150° C. in the case of $CF_3SO_3H$) for 24 hours.

This method has been described by:
e) A. de Angelis, C. Flego, P. Ingallina, L. Montanari, M. G. Clerici, C. Carati, C. Perego, Catalysis Today 2001, 65, 363-371

Under the reaction conditions, there is clear elimination of water and the immobilization of $CF_3SO_3H$ $H_2O$ on the support surface. However, it was not possible to clarify whether the trifluoromethanesulfonic acid hydrate resides on the support surface in only physically bound (strongly adsorbed) highly dispersed form, or whether the trifluoromethanesulfonic acid with vicinal silanol groups reacts to form true chemical bonds. The principle is outlined in the following scheme:

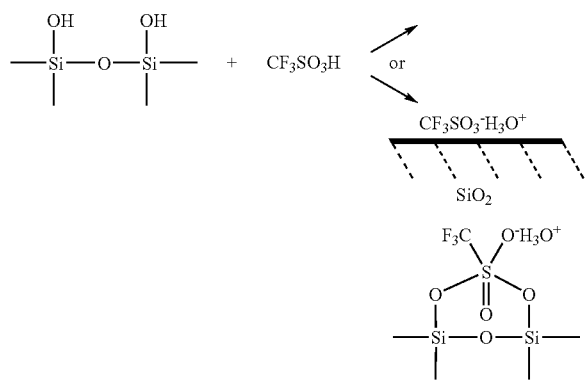

The solid support, preferably silica gel, may also be impregnated at room temperature with the superacid, preferably trifluoromethanesulfonic acid or fluorosulfonic acid.

In this case, the superacid is only bound (adsorbed) physically on the support surface. However, the adsorption is so strong that, in a flow reactor which is charged with a fixed silica gel bed, the superacid, in the case of introduction from the inlet side of the reactor, is bound directly downstream of the inlet only within a thin adsorption zone. This adsorption zone then functions as the catalytic reaction zone. When a continuous reactant stream is introduced from the inlet side into the reactor, this catalytic superacid zone on the fixed bed migrates only very slowly in the direction of the reactant stream, substantially more slowly than the reactant stream itself which is in each case converted to the product stream in the catalytic zone. This method has been described by:

f) R. Mehlberg, R. A. Kretchmer (Amoco Corp.) WO 98/52887
g) Hommeltoft et al. (Topsoe Haldor AS) U.S. Pat. No. 5,245,100
h) Hommeltoft et al. (Topsoe Haldor AS) U.S. Pat. No. 5,220,095

Further variants of the immobilization of superacids, especially of trifluoromethanesulfonic acid, have been described by:

i) E. Benazzi, J. F. Joly (Institut Francais Du Petrole) EP 0 761 306 (1996)
j) F. Chen, A. Guyot, T. Hamaide, C. LeDeore (Exxon) WO 95/26814
k) L. R. Kallenbach, M. M. Johnson (Phillips Petroleum Company) U.S. Pat. No. 5,349,116 (1994)

The carbonylation reactants of the formula (II), as outlined in the scheme which follows, can be prepared in two to three stages from the isoalkylbenzene of the formula (V) which is either commercially available ($R^1=R^4=CH_3$, and also $R^1$=ethyl, $R^4$=methyl) or obtained in a simple manner by Friedel-Crafts alkylation of benzene with commercially available alkyl chloride of the formula (VI) or alternatively by acid-catalyzed electrophilic addition of the alkene of the formula (VII) to benzene.

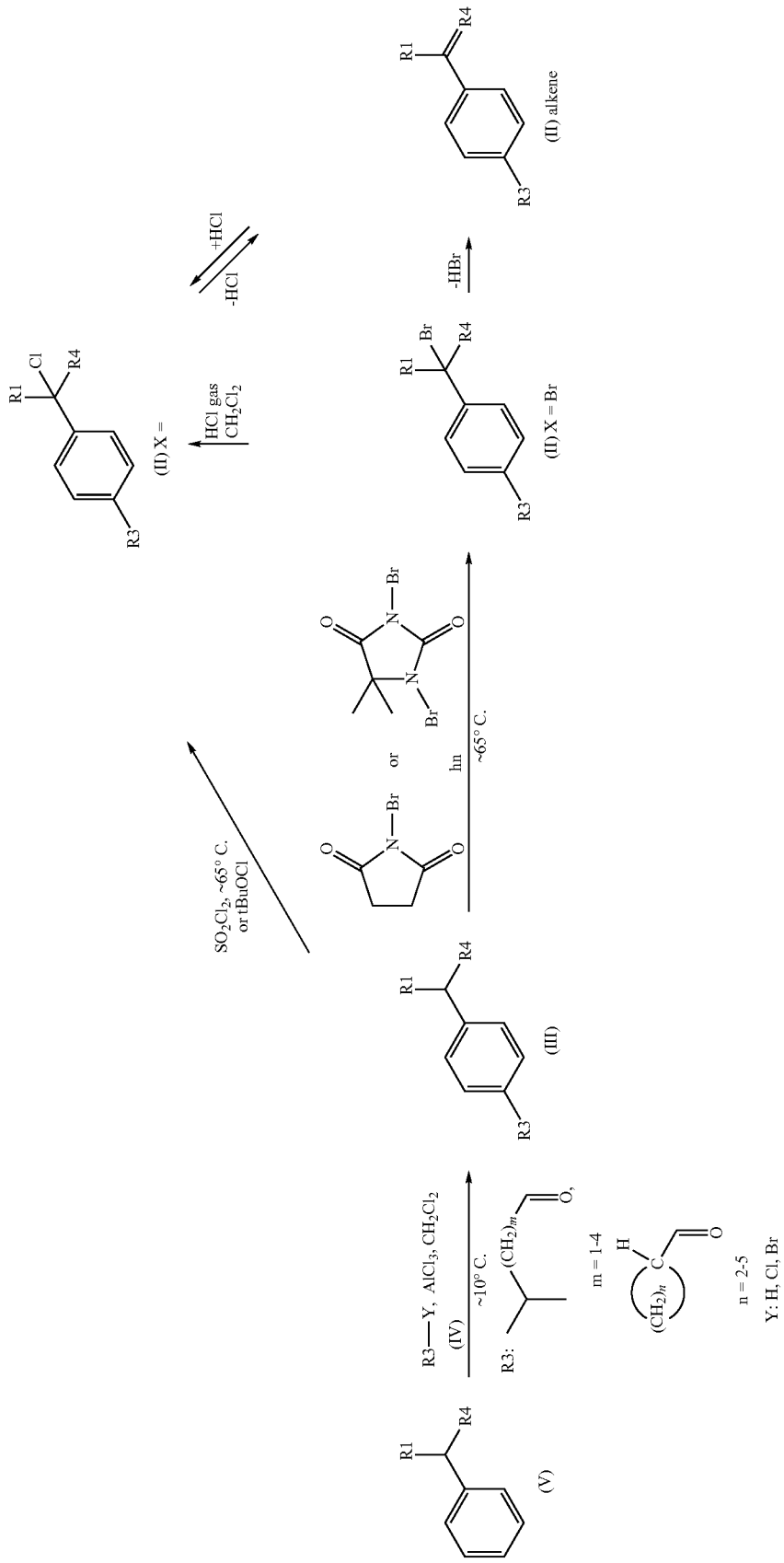

-continued
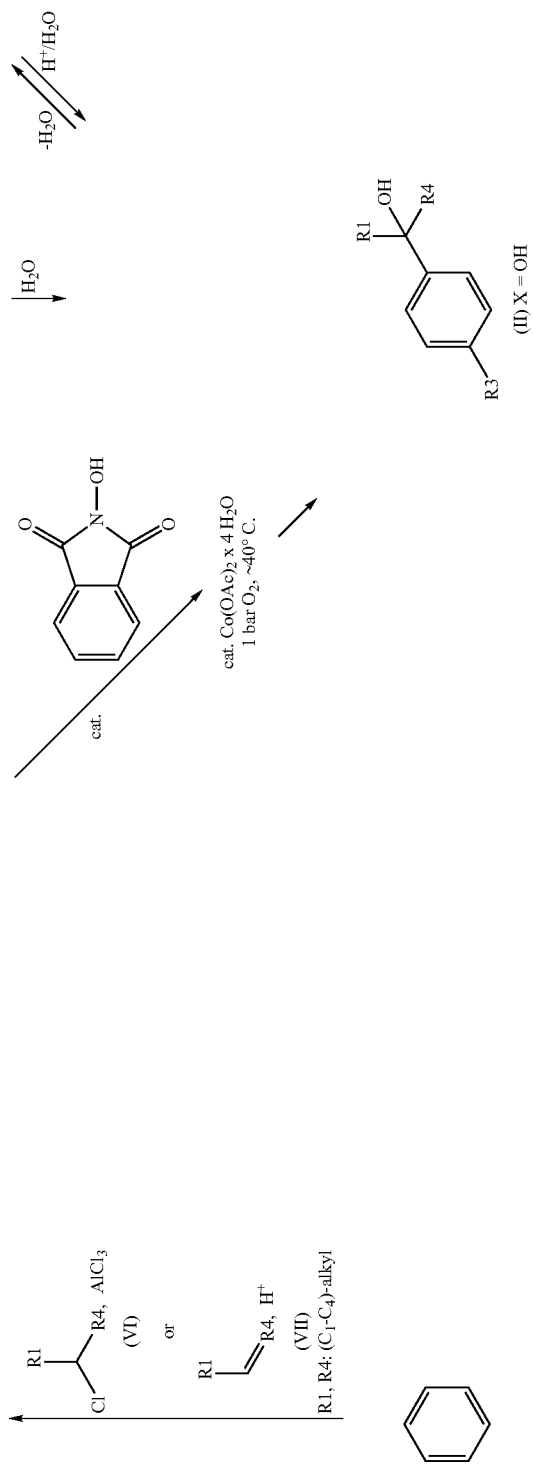

Compounds of the formula (III) are known (WO 95/00480 claim 7, page 179). One example of a Friedel-Crafts acylation of an isoalkylbenzene of the formula (V) (cumene) with an acyl halide of the formula (IV) (4-chlorobutyryl chloride) can be found in WO 95/00480 (Example 1, page 39). The reaction proceeds in good yield with very high para selectivity. The proportion of positional isomers in (III) is only from 0 to 0.2% (see also in reference examples 1 and 2).

Bromides of the formula (II) (X=Br) are known (WO 95/00480, claim 7, page 179). Three embodiments of the benzylic bromination of (III) ($R^1=R^2$=methyl, $R^3$=4-chlorobutyryl) are contained in WO 95/00480 (Example 4, pages 47-49). In the "method A" there (page 47), (III) was heated at reflux with 1.05 equivalents of N-bromosuccinimide (NBS) in carbon tetrachloride in the presence of catalytic amounts of dibenzoyl peroxide (0.13 mol %) for one hour. In the "method B" there (page 48), (III) was heated to 80° C. with 1.045 equivalents of NBS in carbon tetrachloride in the presence of catalytic amounts of 2,2'-azobisisobutyronitrile (AIBN, 8.2 mol %) under a nitrogen atmosphere until the exothermic free-radical chain reaction set in. After 30 minutes at reflux, a further 0.025 equivalent of NBS was added and the mixture was refluxed for a further 15 minutes. In the "method C" there (page 48), a solution of (III) in dichloromethane was admixed with an aqueous solution of sodium bromate ($NaBrO_3$, 0.35 equivalent) and illuminated at 10° C. with stirring. A further 0.70 equivalent of aqueous sodium bromate solution was slowly added dropwise, and the mixture was stirred for another 2 hours and illuminated for a further 30 minutes. Our own experience has shown that all three embodiments are, however, unsuitable for preparative production. Although the desired benzylic bromide was formed as the main component of the reaction mixture in all three cases, the conversion of the reactant was incomplete and three different bromination products were formed primarily. From this mixture, the target product cannot be removed in acceptable purity (for example by crystallization, extraction, vacuum distillation or chromatography) because it is thermally labile (elimination of HBr in the course of heating) and also hydrolyzes readily (formation of the benzylic alcohol and of the alkene by reaction with water; vide infra).

The invention therefore relates to three novel processes which feature a rapid reaction, quantitative conversion of the reactant and clean formation of the target product (see Examples 1A, 1B and 2).

The invention therefore further relates to a process for obtaining bromides of the formula VIII

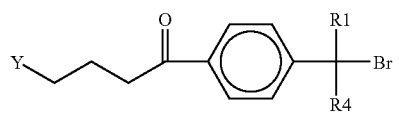

in which Y is a hydrogen, chlorine or bromine atom and R1 and R4 are the same or different and are each independently —($C_1$-$C_4$)-alkyl, which comprises illuminating a compound of the formula III

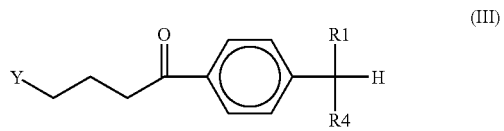

in the presence of N-bromosuccinimide or 1,3-dibromo-5,5-dimethylhydantoin and at the same time heating it.

Preference is given to using a compound of the formula III in which Y is a chlorine atom and R1 and R4 are each methyl.

In this process, the use of a chemical free-radical chain initiator is not necessary, the initiation of the free-radical chain is effected by illumination, the reactant (III, R1=R4=methyl, R3=CO($CH_2$)$_3$—Y) is converted quantitatively and the product of the formula (VIII) is formed in good purity (92 to 98% purity by GC and $^1$H NMR analysis). A further feature of the first process is that the solution of the reactant/suspension of the NBS reagent (1.02-1.10 equiv., preferably 1.03-1.07 equiv.) is heated to about 65° C. in an inert nonpolar solvent, preferably chlorobenzene, with illumination using a sunlight lamp. As soon as the exothermic free-radical chain reaction has started up, the lamp is removed and the further increase of the reaction temperature is restricted by cooling.

In the second process, the solution of the reactant/suspension of the 1,3-dibromo-5,5-dimethylhydantoin reagent (0.51 to 0.54 molar equivalent, preferably 0.52 to 0.53 molar equivalent) is heated to about 65° C. in an inert nonpolar solvent, preferably chlorobenzene, with illumination using a sunlight lamp. As soon as the exothermic free-radical chain reaction has started up, the lamp is removed and the further increase in the reaction temperature is restricted by cooling.

The invention further relates to a process for obtaining bromides of the formula VIII

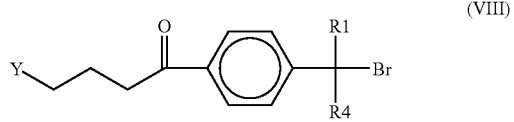

in which Y is a hydrogen, chlorine or bromine atom and R1 and R4 are the same or different and are each independently —($C_1$-$C_4$)-alkyl, which comprises illuminating a compound of the formula III

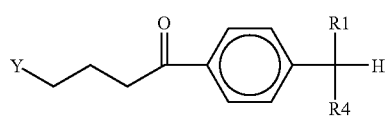

in an aqueous biphasic mixture, the aqueous phase comprising a bromine salt and the second phase consisting of a liquid which is insoluble or only sparingly soluble in water.

It is also possible to meter aqueous hydrobromic acid into the aqueous phase. In addition, the biphasic mixture may also be mixed efficiently, for example by stirring. The $Br_2$ formed in situ by comproportionation is extracted under these conditions continuously into the methylene chloride phase, where it dissociates owing to the illumination to bromine radicals which bring about the benzylic bromination of the reactant (III).

This third process for synthesizing the bromide (VIII) is advantageous on the large scale because it affords the product in high yield and purity and does not generate any further costs resulting from the combustion of intermediates.

Preference is given to using a compound of the formula III in which Y is a chlorine atom and R1 and R4 are each methyl.

Suitable lamps should radiate light with a frequency which is suitable for dissociating $Br_2$ to bromine radicals. Suitable light is, for example, in the range from visible light to ultraviolet light, as radiated by a low-pressure mercury lamp, for example Original Hanau TQ150. Optionally, it is possible to use filters which are transparent to the somewhat low-frequency light fraction which is required to cleave the Br—Br bond, but opaque to the somewhat higher-frequency light fraction which might bring about the cleavage of the bond between benzylic carbon atom and bromine atom of the reaction product (VIII).

Suitable bromine salts are potassium bromate, sodium bromate, barium bromate, preferably sodium bromate.

Suitable liquids which are insoluble or only sparingly soluble in water are, for example, dichloromethane, carbon tetrachloride, 1,2-dichloroethane, various frigens, chlorobenzene, fluorobenzene or α,α,α-trifluorotoluene. Preference is given to dichloromethane. Since the reactants of the formula (III) and the products [bromides of the formula (VIII)] are also insoluble or only sparingly soluble in water and frequently have low melting points in the range from 0 to 50° C., and there is an interest in carrying out the reaction with minimum use of solvent (i.e. at maximum space-time yield), the reactant itself may also function as the suitable liquid. In that case, either only the minimum amount of solvent which is required to liquefy the reactant is added, or operation is effected entirely without organic solvent and the reaction temperature is selected in such a way that the reactant is just present in molten form (as a liquid phase).

The solubility of the suitable liquid is less than 50 g per liter of water at 20° C. The amount of sodium bromate is from 1.0 mol to 10.0 mol of $NaBrO_3$ per liter of water, preferably from 2.7 mol to about 7.5 mol of $NaBrO_3$ per liter of water, more preferably from 5.0 to 7.5 mol of $NaBrO_3$ per liter of water. These data relate to the amount of water initially charged from the start and do not include the water which is added in the course of metering of the aqueous hydrobromic acid. Up to a concentration of about 4 mol/l, the sodium bromate is dissolved in water to form a clear solution. At higher concentrations, a suspension is present which dissolves in the course of the reaction because sodium bromate is consumed by the comproportionation reaction with HBr to form $Br_2$. From 0.3 mol of 0.4 mol of bromate is used per mole of reactant of the formula (III), preferably about 0.34 mol.

The term "aqueous biphasic mixture" refers to a mixture of two liquids, one liquid being water and the second liquid being a liquid which is insoluble or only sparingly soluble in water. When the reaction is carried out in the presence of little water, undissolved bromate is present at the start as a further solid phase. Owing to the consumption of bromate, this solid dissolves in the course of the reaction. The aqueous biphasic mixture generally does not comprise any further solid/liquid phase boundary. However, it is possible that flocculations occur at low temperatures and high concentrations of the compounds of the formulae III or VIII. The aqueous biphasic mixture is stirred or mixed by customary methods so that good distribution of the phases is ensured.

The hydrogen bromide may either be added as an aqueous solution, preferably as a 48% aqueous solution, or in gaseous form. An amount of 1.00 mol to 1.20 mol of HBr per mole of reactant of the formula (III) is added, preferably about 1.15 mol.

The amounts of water and liquid which is insoluble or only sparingly soluble in water which are used may vary within wide ranges and can be determined readily by those skilled in the art.

The reaction temperature is from −15° C. to +70° C., preferably from −5° C. to +10° C., more preferably from −2° C. to +2° C.

At a temperature of 0° C., the reaction time is generally from 10 to 60 minutes. The metering time of the hydrobromic acid and thus also the entire reaction time depend mainly on the available cooling capacity, i.e. on the rate with which the heat of reaction and the radiant heat of the illumination lamp(s) can be removed from the reaction vessel.

Chlorides of the compound of the formula (II) (X=Cl) are known (WO 95/00480 claim 7, page 179). One method of formation is described in (WO 95/00480 (Example 4, method D, page 49). In this method, HCl gas was bubbled through the solution of the mixture of 67% by weight of the benzylic bromide of the formula (VIII) (Y=Cl) and 18% by weight of the corresponding alkene for 70 minutes and a 3:1 mixture of the benzylic bromide (X=Br) and of the benzylic chloride (X=Cl) was obtained.

The invention further provides a process for preparing chlorides of the formula (IX) in a preparatively useful way.

The invention therefore further relates to a process for obtaining chlorides of the formula IX

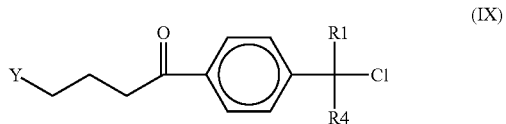

in which Y is a hydrogen, chlorine or bromine atom and R1 and R4 are the same or different and are each independently —($C_1$-$C_4$)-alkyl, which comprises reacting a compound of the formula III

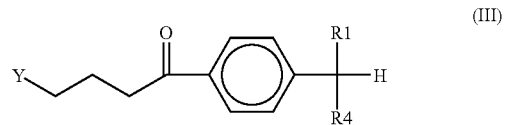

in which Y is a hydrogen, chlorine or bromine atom and R1 and R4 are the same or different and are each independently —($C_1$-$C_4$)-alkyl to give a cyclopropyl keto derivative of the formula IIIa

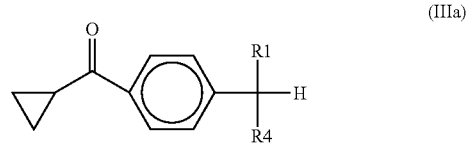

then free-radically chlorinating it, in the benzylic position, with sulfuryl chloride or with tert-butyl hypochlorite, and finally converting it to the compound of the formula IX.

Preference is given to using a compound of the formula III in which Y is a chlorine atom and R1 and R4 are each methyl.

In these processes, the reactant of the formula (III) ($R^1=R^2$=methyl, $R^3$=CO(CH$_2$)$_3$—Y) is converted under the action of base, such as inorganic bases, preferably sodium hydroxide solution, to the cyclopropyl keto compound of the formula IIIa as an intermediate. The compound of the formula IIIa is then free-radically chlorinated in the benzylic position with sulfuryl chloride or alternatively with tert-butyl hypochlorite. The benzyl chloride compound obtained is then reacted with an acid, for example hydrogen chloride, to give a compound of the formula IX. The chain can be initiated either by illumination of the reaction mixture or with a catalytic amount of dibenzoyl peroxide or AIBN. Examples 82 to 90 illustrate the performance of this synthesis variant by way of example.

According to M. J. Mintz, C. Walling Org. Synth. 49, 9, (1969), tert-butyl hypochlorite is obtained by adding a solution of tert-butanol in glacial acetic acid dropwise to aqueous chlorine bleaching liquor. The benzylic free-radical chlorination of cumene with sulfuryl chloride has been described in M. S. Kharasch, H. C. Brown J. Am. Chem. Soc. 1939, 61, 2142-2150; G. A. Russell, H. C. Brown J. Am. Chem. Soc. 1955, 77, 4031-4035.

Alkenes of the formula (II) (X and R4 together form a C═C double bond) are known (WO 95/00480 claim 11, page 181). Preparation processes are outlined in WO 95/00480 in scheme C (page 50) (see also Example 54).

A further aspect of the invention relates to compounds of the formula X

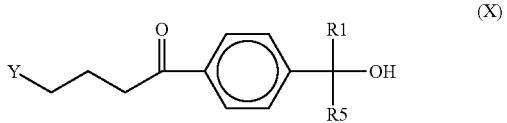

where Y is a hydrogen, chlorine or bromine atom and

R1 and R5 are the same or different and are each independently —(C$_1$-C$_4$)-alkyl.

The invention further relates to compounds of the formula X in which Y is a chlorine atom and R1 and R5 are each methyl.

The invention further relates to a process for obtaining compounds of the formula X, which comprises a) reacting a compound of the formula III

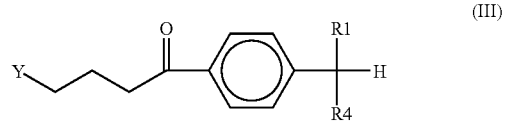

where Y is a hydrogen, chlorine or bromine atom and R1 and R4 are the same or different and are each independently —(C$_1$-C$_4$)-alkyl with oxygen in the presence of cobalt(II) acetate tetrahydrate and N-hydroxyphthalimide or b) reacting a compound of the formula XI

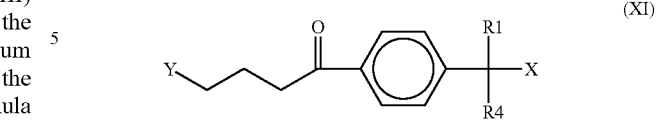

where Y is a hydrogen, chlorine or bromine atom,

X is a chlorine or bromine atom,

R1 and R4 are the same or different and are each independently —(C$_1$-C$_4$)-alkyl or R4 and X together are a C═C double bond with water.

Benzylic alcohols of the formula (II) (X═OH) are novel. According to the above scheme, they may be prepared by direct, benzylic free-radical oxidation of compounds of the formula (III), in which case the oxidizing agent used is oxygen at standard pressure, and the catalysts used are cobalt(II) acetate tetrahydrate and N-hydroxyphthalimide (see also Example 27).

The closely related benzylic oxidation of cumene by the same method has been described by F. Minisci et al., Proc. Res. & Dev. 2004, 8, 163-168. Alternatively, the alcohols of the formula (II) (X═OH) can also be prepared hydrolytically from the bromides of the formula (II) (X═Br) (see also Example 28). The alcohols of the formula (II) (X═OH) can also be obtained analogously from the chlorides of the formula (II) (X═Cl), either by direct hydrolysis or via the alkene as an intermediate.

EXAMPLES

The invention is illustrated in detail below with reference to examples. End products are determined generally by $^1$H NMR (400 MHz, in CDCl$_3$ or DMSO-d$_6$). Temperature data are in degrees Celsius, RT means room temperature (22° C. to 26° C.), min means minute. Abbreviations used are either explained or correspond to the customary conventions. The carbonylation screening experiments were carried out in a reactor block which consisted of eight 2 ml stainless steel autoclaves. The eight miniautoclaves of one block are referred to as A1 to A8 in the examples which follow. Each of these miniautoclaves was equipped with a cross-shaped 9×9 mm magnetic stirrer bar. The displacement of the air from the gas and liquid phase ("purging") was effected in a fully automated manner, controlled by software. In the course of this, the CO reaction gas was injected three times at in each case 5 bar and the autoclave was then evacuated in each case to a slight vacuum (to about 0.5 bar). The preparative carbonylation experiments were carried out in a 500 ml Büchi autoclave made of Hasteloy which contained a sparging stirrer. The sparging stirrer was adjusted to a rotation rate of 1000 revolutions/minute.

Reference Example 1

Synthesis of 4-chloro-1-(4-isopropylphenyl)butan-1-one (Formula III, $R^1=R^2$=methyl, $R^3$=4-chlorobutyryl) from isopropylbenzene (cumene)

A 2 l four-neck flask with mechanical blade stirrer was initially charged under an N$_2$ atmosphere with 166.70 g (1.25 mol) of aluminum chloride and 605.14 g (455 ml) of dichloromethane. 176.33 g (139.9 ml, 1.25 mol) of 4-chlorobutyryl chloride were metered into this suspension at an internal temperature of +10° C. within 30 minutes. Subsequently, 142.73 g (166 ml, 1.187 mol) of cumene were added dropwise at 10° C. within 40 minutes. In the course of this, HCl gas escaped. The mixture was stirred at +10° C. for a further 45 minutes. After as early as 5 minutes, the conversion was complete. The yellow reaction solution was metered into 1000 g of ice-water within 90 minutes. The mixture was stirred at 0-+5° C. for a further 30 minutes. During a further continued stirring time of 90 minutes, the mixture warmed to RT. The phases were separated. The aqueous phase was extracted at RT twice more with 532 g (400 ml) each time of dichloromethane. The combined organic phases were washed at 20° C. once with 412.10 g (400 ml) of 5% sodium hydrogencarbonate solution. The dichloromethane phase was concentrated under reduced pressure as far as possible at a bath temperature of 30° C. on a rotary evaporator. 280.3 g of yellow oil were obtained. The mixture was taken up in 240.60 g (280 ml) of 2:1 isopropanol/water mixture, cooled to 0° C. and stirred at 0° C. for a further 2 hours. After only about 5 minutes, the crystallization from the milky opaque emulsion began at 0° C. The crystalline product was filtered off with suction using a suction filter and washed with 128.60 g (150 ml) of 2:1 isopropanol/water mixture. The solid was dried under $N_2$ blanketing at RT under reduced pressure. 253.4 g (1.128 mol, 95.0% of theory) of fine, colorless, flake-shaped crystals, HPLC purity 98.8%, melting point (m.p.) 38-39° C. were obtained. $^1$H NMR ($CDCl_3$): δ=1.28 (d, 6H, 2×$CH_3$), 2.23 (qui, 2H, $CH_2$), 2.98 (sept, 1H, CH), 3.16 (t, 2H, $CH_2$), 3.68 (t, 2H, $CH_2$), 7.32 (~d, 2H, arom.-H), 7.91 (~d, 2H, arom.-H). MS (Cl+, solvent (sol.) methanol (MeOH): m/z=227/225 (11%/33%, M+H$^+$), 189 (10%, M+H$^+$ —HCl), 162 (21%, M+H$^+$ —$CH_2CH_2Cl$), 147 (100%, M+H$^+$ —$CH_2CH_2CH_2Cl$). IR (Kbr): v=1678 (C=O), 1600 (C=C of aryl), 1223 cm$^{-1}$.

Reference Example 2

Synthesis of 4-chloro-1-(4-isopropylphenyl)butan-1-one (formula III, $R^1$=$R^2$=methyl, $R^3$=4-chlorobutyryl) from isopropylbenzene (cumene)

A 2 l four-neck flask with mechanical blade stirrer was initially charged under an $N_2$ atmosphere with 138.0 g (1.03 mol) of aluminum chloride and 1000 ml of dichloromethane. At an internal temperature of +5° C., 142.4 g (113 ml, 1.25 mol) of 4-chlorobutyryl chloride were metered into this suspension under ice cooling within 10 minutes. Subsequently, 120.2 g (139 ml, 1.00 mol) of cumene were added dropwise to the almost clear yellow solution within 35 minutes. As increasing evolution of HCl gas set in, after half of the time, the ice bath was replaced by a water bath, so that RT was attained after 20 min. The mixture was left to stir for a further 30 min. The yellow reaction solution was metered into 1000 g of ice-water within 90 minutes with stirring. The organic phase was removed and the aqueous phase was extracted once more with 2×200 ml of dichloromethane. The combined organic phases were washed with 300 ml of 5% sodium hydrogencarbonate solution. The dichloromethane phase was concentrated as far as possible on a rotary evaporator at a bath temperature of 30° C. under reduced pressure, and the yellow oil was taken up in 200 ml of n-heptane and again concentrated as far as possible under reduced pressure. The residue was dissolved at RT in 225 ml of n-heptane under an $N_2$ atmosphere to give a clear solutuion. The solution was cooled slowly and seeded. At about 19° C., the crystallization commenced. When +2° C. were attained, a thick crystal slurry had formed which was stirred for a further 10 minutes and subsequently filtered with suction through a slightly precooled glass frit. The crystals were washed with ice-cold n-heptane until the mother liquor had been fully washed out of them. They were filtered off under strong suction and the solid was dried under high vacuum. 182.8 g of colorless crystals (97.7 area % by GC, m.p. 38° C.) and 37.8 g of yellow oil from the concentration of the mother liquor were obtained. Crystallization of the oil from 40 ml of n-heptane afforded a further 12.7 g of colorless crystals (97.7 area % by GC, m.p. 38° C.). Total yield: 195.5 g (870 mmol, 87% of theory). The spectra were identical to the product from reference example 1.

GC system (FID): 30 m HP1 fused silica capillary column, 0.53 mm ID, 1.5 μm layer thickness of the stationary phase, column flow rate: 8.5 ml of He/min; temperature program started at 50° C., isothermal for 2 min, then to 275° C. at 20° C./min; $t_{ret}$ product=11.3 min, isomer 11.0 min, cumene 5.3 min.

Example 1A

Synthesis of 1-[4-(1-bromo-1-methylethyl)phenyl]-4-chlorobutan-1-one (Formula VIII, Y=Cl) of High Purity with N-bromosuccinimide (NBS) Under Illumination In a 50 ml three-neck sulfonation flask with stirrer bar, thermometer and reflux condenser, 2.30 g (10.0 mmol) of 4-chloro-1-(4-isopropylphenyl)-butan-1-one (97.9%, from reference example 2) and 1.93 g (10.8 mmol) of N-bromosuccinimide (99%, from ABCR) were dissolved/suspended under $N_2$ in 33 ml of carbon tetrachloride (from Merck Darmstadt). The flask was immersed up to about half its height into an oil bath which had been preheated to 80° C., and irradiated from above at an oblique angle with an Osram Ultra Vitalux lamp which had about 10 cm of separation from the surface of the suspension. From about 60° C., the distinctly exothermic free-radical chain reaction set in with foaming. After the chain had been initiated, the warm oil bath was immediately lowered. The reaction temperature of from 60° C. to 75° C. was maintained by the heat of reaction and the heat radiated by the lamp. The heavy NBS was converted to the light succinimide which floated as a white solid on the surface of the suspension. After 5 minutes, the reactant had already been converted to an extent of >99% according to GC analysis of a sample. After 15 min, the lamp was switched off and the reaction mixture was allowed to cool to RT. The succinimide was filtered off with suction and washed with a little $CCl_4$. The filtrate was washed with 3×11 ml of cold water and concentrated under reduced pressure. The oily residue was seeded with a crystal of the product, whereupon crystallization set in, and dried further under high vacuum. 2.93 g (9.65 mmol, 96% of theory) of pale beige crystals, melting point from 35.5 to 36.5° C., were obtained. In the course of GC analysis (system as in reference example 2), the product eliminated HBr to a very substantial extent and was detected as the alkene of the formula II ($t_{ret}$ 11.6 min, 94.5 area %). The GC analysis is suitable for a rough determination of purity. In the course of HPLC analysis of the bromide, solvolysis proceeded to a substantial extent, predominantly to the alcohol (X) (Y=Cl) and to the alkene of the formula II. The extent of the solvolysis and precise composition of the solvolysis products was dependent upon the preparation of the HPLC sample and upon the lifetime of the solution before the injection. The HPLC analysis is therefore unsuitable even for a rough determination of purity. At best, the purity is determined by H NMR ($CDCl_3$) by evaluating the intensified integrals of the products, of the =$CH_2$ protons of the alkene (2×s, 2×1H, δ=5.21 and 5.49), and of the $CH_2Br$ protons (2×d, 2×1H, δ=4.13 and 4.37) and of the $CH_3$ protons (s, 3H, δ=2.34) of the dibromide. It was thus determined that the product was 97.5 mol % pure, and contained 1.6 mol % of the dibromide, 0.9 mol % of the alkene and 0 mol % of the reactant. In the $^{13}$C NMR, no impurities were found.

$^1$H NMR (CDCl$_3$): δ=2.20 (s, 6H, 2×CH$_3$), 2.23 (qui, 2H, CH$_2$), 3.17 (t, 2H, CH$_2$), 3.68 (t, 2H, CH$_2$), 7.71 (~dt, 2H, arom. H), 7.94 (~dt, 2H, arom. H). $^{13}$C NMR (CDCl$_3$): d=26.87 (CH$_2$), 35.33 (2×CH$_3$), 35.47 (CH$_2$CO), 44.75 (CH$_2$Cl), 62.44 (c-Br), 126.25 (2× arom. CH), 128.22 (2× arom. CH), 135.99 (arom. C), 151.89 (arom. C), 198.39 (C=O). IR (solid): v=1679 (C=O), 1604 (C=C of aryl), 1409, 1227, 1092, 842, 776, 738, 728, 612 cm$^{-1}$.

Example 1B

Synthesis of 1-[4-(1-bromo-1-methylethyl)phenyl]-4-chlorobutan-1-one (formula VIII, Y=Cl) with 1,3-dibromo-5,5-dimethylhydantoin in Chlorobenzene with Illumination In a 50 ml three-neck sulfonation flask with stirrer bar, thermometer and reflux condenser, 2.30 g (10.0 mmol) of 4-chloro-1-(4-isopropylphenyl)-butan-1-one (97.9%, from reference example 2) and 1.54 g (5.3 mmol) of 1,3-dibromo-5,5-dimethylhydantoin (98%, Aldrich) were dissolved/suspended under N$_2$ in 33 ml of chlorobenzene (from Merck Darmstadt). The flask was immersed up to about half its height into an oil bath which had been preheated to 63° C., and irradiated from above at an oblique angle with an Osram Ultra Vitalux lamp which had about 10 cm of separation from the surface of the suspension. From about 58° C., the distinctly exothermic free-radical chain reaction set in, which caused the internal temperature to rise slowly further up to 69° C. within about 5 min in order then to fall again. After a total of about 10 minutes of reaction time, the oil bath was removed and the lamp switched off. According to GC analysis of a sample, the reactant had been converted quantitatively and the alkene was indicated at 92 area percent (area %). The yellow, slightly opaque solution cooled to RT was washed with 3×10 ml of cold water, concentrated under reduced pressure and dried under high vacuum. The oily residue was seeded with a crystal of the pure product, whereupon crystallization set in. The product was dried further under high vacuum. 3.04 g (10.0 mmol, 100% of theory) of pale beige crystals, melting point from 35° C. to 36.5° C. were obtained. GC analysis (system as in reference example 2) showed 95.1 area % of alkene. Analysis by $^1$H NMR, as described in Example 1, gave 94 mol % of the desired product, 3 mol % of the dibromide and 3 mol % of the alkene.

Example 2A

Synthesis of 1-[4-(1-bromo-1-methylethyl)phenyl]-4-chlorobutan-1-one (formula VIII, Y=Cl) in a Biphasic Methylene Chloride/Water Mixture with Illumination and In Situ Generation of Bromine by Comproportionation of Sodium Bromate and Hydrogen Bromide The reaction was carried out in a concentric, cylindrical 250 ml 4-neck illumination apparatus (glass) with magnetic cross, intensive cooler, peristaltic pump, PT100 heat sensor and nitrogen blanketing. In the center of the cylinder was disposed an immersed UV lamp (TQ150, Original Hanau) which was cooled by means of a cryostat (Julabo type FP 40, 50:50 ethanol/water mixture).

The illumination apparatus was initially charged with 5.21 g (33.84 mmol) of 98% sodium bromate and 12.5 ml of water and dissolved with stirring. The solution was blanketed with nitrogen. 22.79 g (99.28 mmol) of 4-chloro-1-(4-isopropylphenyl)butan-1-one (97.9 area %) and 110 ml of dichloromethane were added. The UV lamp, precooled to 0° C., was installed and switched on. In addition, the illumination apparatus was cooled externally with a dry ice/ethanol mixture. After an internal temperature of 0° C. had been attained, the metered addition (by peristaltic pump) of 19.64 g (116.50 mol) of 48% aqueous hydrobromic acid solution was commenced. This was metered in within 23 minutes. In the course of this, the reaction solution warmed to 2° C. The lines of the peristaltic pump were flushed with 5 ml of water. After the metered addition of HBr had ended, the lamp was operated further for a further 15 min to complete the reaction. The reaction solution was opaque and colorless. It was transferred to a separating funnel and the phases were separated after a phase separation time of 10 min. The lower phase (DCM) weighed 173.3 g; the upper phase (water) weighed 32.4 g.

The organic phase was washed with 2×50 ml of water. The organic phase (163.7 g) was concentrated on a rotary evaporator at water bath temperature 30° C. up to an end vacuum of 20 mbar. At the same time, azeotropic drying was also effected. This resulted in 29.04 g of a clear, virtually colorless oil which crystallized fully.

GC analysis: 0.5 area % of reactant (tret 14.54 min), 98.5 area % of product (of which 97.8 area % detected as the alkene, tret 14.87 min and 0.7 area % as the bromide, tret 15.45 min), 1.0 area % of dibromide (tret 16.00 min). 29.04 g (98.5 area %=28.6 g of 100% product) corresponds to a yield of 94.9% of theory. The spectra corresponded to the data described in Example 1A.

Example 2B

Synthesis of 1-[4-(1-bromo-1-methylethyl)phenyl]-4-chlorobutan-1-one (Formula VIII, Y=Cl) in an Initial Triphasic Mixture (Methylene Chloride/Water and Undissolved, Solid Sodium Bromate) with Illumination and In Situ Generation of Bromine by Comproportionation of Sodium Bromate and Hydrogen Bromide The reaction was carried out in a concentric, cylindrical 250 ml 4-neck illumination apparatus (glass) with magnetic cross, intensive cooler, peristaltic pump, PT100 heat sensor and nitrogen blanketing. In the center of the cylinder was disposed an immersed UV lamp (TQ150, Original Hanau) which was cooled to from −6 to −10° C. by means of a cryostat (Lauda RM6, 50:50 ethanol/water mixture).

In the illumination apparatus, 10.30 g (67.9 mmol) of 99.5% sodium bromate were suspended in 12.5 ml of water and dissolved partly with stirring. The suspension was blanketed with nitrogen. 45.40 g (202.0 mmol) of 4-chloro-1-(4-isopropylphenyl)butan-1-one (98.4 area %, GC) and 85 ml of dichloromethane were added, whereupon the reactant dissolved immediately. The stirred emulsion/suspension was sparged with argon in order to drive out dissolved oxygen and then cooled to −7° C. with an ice/sodium chloride bath (−15° C.). The UV lamp was switched on and 25.5 ml (225.0 mmol) of 48% aqueous hydrogen bromide solution were metered in by peristaltic pump within 15 minutes, in the course of which the reaction temperature rose to a maximum of +0.5° C. Directly after the end of the dropwise addition, the sodium bromate solid had disappeared fully and the liquid phases were no longer brown-colored. After the end of the dropwise addition, illumination was continued for another 2 minutes, then the lamp was switched off. The liquid biphasic mixture was transferred into a separating funnel, the phases were separated and the lower organic phase was washed again with 3×25 ml of water. The organic phase was concentrated under reduced pressure with azeotropic drying on a rotary evaporator; the oily residue was dried under high vacuum. Seeding resulted in rapid, full crystallization. 61.05 g of colorless crystals were obtained.

GC analysis: 2.1 area % of reactant, 95.0 area % of product, 0.9 area % of dibromide.

61.05 g (95.0 area %=58.0 g of 100% product) corresponds to a yield of 94.6% of theory. The spectra corresponded to the data described in Example 1A.

Evaluation of the $^1$H NMR integral gave 93.1 mol % of desired bromide, 1.9 mol % of olefin, 2.7 mol % of dibromide and 2.3 mol % of unconverted reactant.

Examples 3-10

Synthesis of 2-[4-(4-chlorobutyryl)phenyl]-2-methylpropionic acid (Formula I, $R^1=R^2$=methyl; $R^3$=4-chlorobutyryl) by Carbonylation of the Bromide (VIII, Y=Cl) in Superacid or in Concentrated Sulfuric Acid at 40° C. in the Presence of Preformed Copper(I) Tricarbonyl Ion as an Additive 3.0 mg (0.0419 mmol, 22.8 mol % based on the reactant) of $Cu_2O$ were weighed into each of the eight miniautoclaves (A1 to A8). The mini-autoclaves were installed into the reactor block and sealed. The autoclaves were purged and charged in an argon countercurrent, by means of inertized GC vials, with 0.5 ml of the particular solvent (A1 to A6 with 98% trifluoromethanesulfonic acid $CF_3SO_3H$ from Aldrich; A7 and A8 with 96% sulfuric acid from Merck Darmstadt). The miniautoclaves were each sealed with a gas-tight septum and purged again, and the carbon monoxide reaction gas was injected up to the desired pressure (5 bar for A1 and A2, 25 bar for A3 and A4, 40 bar for A5 and A6, 60 bar for A7 and A8). The reaction block was heated to the reaction temperature of 40° C. with magnetic stirring of the miniautoclaves (200 revolutions/min). In the following 30-minute preformation phase, reaction of the $Cu_2O$ with CO formed the $[Cu(CO)_3]+$ additive in situ. Within this period, the reactant solution was prepared. To this end, 1.12 g (3.68 mmol) of 1-[4-(1-bromo-1-methylethyl)phenyl]-4-chlorobutan-1-one (from Example 2) were weighed into a 2.5 ml standard flask and made up to the mark with about 1.4 ml of carbon tetrachloride to form a clear solution. After the preformation phase had ended, in each case 125 µl (0.184 mmol) of the reactant solution were syringed by means of a pressure-tight glass syringe through the septum into each of the eight miniautoclaves manually within in each case 1 minute. On completion of the reactant addition, the reaction time of 4.0 hours commenced. Only at the start of the reaction was the CO gas injected precisely up to the intended pressure. In the course of the carbonylation, the internal autoclave pressure falls off somewhat as a result of CO consumption. The process is thus not isobaric. After the reaction time had ended, the reactor block was cooled to 25° C. and decompressed.

The autoclaves were deinstalled and the mixtures were taken up in 2.0 ml each of ice-water. The aqueous opaque mixture was extracted in each case with 2×2.0 ml of carbon tetrachloride. The organic (lower) phase was in each case removed quantitatively and made up to precisely 10 ml with carbon tetrachloride. Of the thus obtained clear solution, precisely 1.0 ml was pipetted into a GC vial. The sample was dried at RT in a nitrogen stream and the resulting residue was dissolved in acetonitrile. The solution was analyzed by means of HPLC (column: Zorbax Eclipse XDB-C8 150×4.6 mm; temperature: 25° C., solvent A: 20 mM triethylamine/pH 7.0 acetic acid buffer; solvent B: 100% acetonitrile; linear gradient program: t=0 A:B=90:10, t=15 min A:B=10:90; t=25 min A:B=10:90; flow rate: 1 ml/min; detection: UV at 254 nm; injection volume: 5.0 µl). The yields were calculated from the peak areas of the expected carboxylic acid ($t_{ret}$=7.26 min) by the external standard method, and the measured peak areas were compared with a calibration line. The calibration line was determined beforehand from defined amounts of the authentic carboxylic acid. The reaction parameters and calculated yields are compiled in the table:

| Autoclave No. | Reactant [mmol] | Additive [mmol] | Acid 0.5 ml | CO pressure [bar] | Temp. [° C.] | Yield (I) [% of theory] |
|---|---|---|---|---|---|---|
| A1 | bromide 0.184 | $Cu_2O$ 0.0419 | $CF_3SO_3H$ | 5 | 40 | 47 |
| A2 | bromide 0.184 | $Cu_2O$ 0.0419 | $CF_3SO_3H$ | 5 | 40 | 40 |
| A3 | bromide 0.184 | $Cu_2O$ 0.0419 | $CF_3SO_3H$ | 25 | 40 | 72 |
| A4 | bromide 0.184 | $Cu_2O$ 0.0419 | $CF_3SO_3H$ | 25 | 40 | 73 |
| A5 | bromide 0.184 | $Cu_2O$ 0.0419 | $CF_3SO_3H$ | 40 | 40 | 71 |
| A6 | bromide 0.184 | $Cu_2O$ 0.0419 | $CF_3SO_3H$ | 40 | 40 | 61 |
| A7 | bromide 0.184 | $Cu_2O$ 0.0419 | $H_2SO_4$ | 60 | 40 | 0 |
| A8 | bromide 0.184 | $Cu_2O$ 0.0419 | $H_2SO_4$ | 60 | 40 | 0 |

Examples 11-18

Synthesis of 2-[4-(4-chlorobutyryl)phenyl]-2-methylpropionic acid (Formula I, $R^1=R^2$=methyl; $R^3$=4-chlorobutyryl) by Carbonylation of the Bromide (VIII, Y=Cl) in Superacid or in Conc. Sulfuric Acid at 40° C. in the Presence or Absence of Preformed Copper(I) Tricarbonyl Ion as an Additive The carbonylations were carried out as in Examples 3-10. 96% sulfuric acid was used in the autoclaves A1-A4, 98% trifluoromethanesulfonic acid in the autoclaves A5-A8. In the autoclaves A1, A2, A5 and A6, no $Cu_2O$ addition was employed. In all reactions, the reactant was metered in dissolved in $CCl_4$ and at reaction temperature and CO pressure. The results are compiled in the table:

| Autoclave No. | Reactant [mmol] | Additive [mmol] | Acid 0.5 ml | CO pressure [bar] | Temp. [° C.] | Yield (I) [% of theory] |
|---|---|---|---|---|---|---|
| A1 | bromide 0.184 | — | $H_2SO_4$ | 40 | 40 | 0 |
| A2 | bromide 0.184 | — | $H_2SO_4$ | 40 | 40 | 0 |
| A3 | bromide 0.184 | $Cu_2O$ 0.0419 | $H_2SO_4$ | 40 | 40 | 0 |
| A4 | bromide 0.184 | $Cu_2O$ 0.0419 | $H_2SO_4$ | 40 | 40 | 0 |
| A5 | bromide 0.184 | — | $CF_3SO_3H$ | 60 | 40 | 60 |
| A6 | bromide 0.184 | — | $CF_3SO_3H$ | 60 | 40 | 62 |
| A7 | bromide 0.184 | $Cu_2O$ 0.0419 | $CF_3SO_3H$ | 60 | 40 | 66 |
| A8 | bromide 0.184 | $Cu_2O$ 0.0419 | $CF_3SO_3H$ | 60 | 40 | 56 |

Examples 19-26

Synthesis of 2-[4-(4-chlorobutyryl)phenyl]-2-methylpropionic acid (Formula I, $R^1=R^2$=methyl; $R^3$=4-chlorobutyryl) by Carbonylation of the Bromide (VIII, Y=Cl) in Superacid at 0° C. in the Presence or Absence of Preformed Copper(I) Tricarbonyl Ion as an Additive The carbonylations were carried out as in Examples 3-10, but with cooling of the reactor block to 0° C. In the autoclaves A1, A2, A5 and A6, no $Cu_2O$ addition was employed. In all reactions, the reactant was metered in, dissolved in $CCl_4$ and at 0° C. and CO pressure. The results are compiled in the table:

| Autoclave No. | Reactant [mmol] | Additive [mmol] | Acid 0.5 ml | CO pressure [bar] | Temp. [° C.] | Yield (I) [% of theory] |
|---|---|---|---|---|---|---|
| A1 | bromide 0.184 | — | $CF_3SO_3H$ | 25 | 0 | 69 |
| A2 | bromide 0.184 | — | $CF_3SO_3H$ | 25 | 0 | 60 |
| A3 | bromide 0.184 | $Cu_2O$ 0.0419 | $CF_3SO_3H$ | 25 | 0 | 70 |
| A4 | bromide 0.184 | $Cu_2O$ 0.0419 | $CF_3SO_3H$ | 25 | 0 | 52 |
| A5 | bromide 0.184 | — | $CF_3SO_3H$ | 40 | 0 | 75 |
| A6 | bromide 0.184 | — | $CF_3SO_3H$ | 40 | 0 | 74 |
| A7 | bromide 0.184 | $Cu_2O$ 0.0419 | $CF_3SO_3H$ | 40 | 0 | 60 |
| A8 | bromide 0.184 | $Cu_2O$ 0.0419 | $CF_3SO_3H$ | 40 | 0 | 50 |

In all reactions, the HPLC peak of the desired carboxylic acid had >95 area % of all peaks. In the case of the product in the autoclaves A5 and A6, the HPLC peak of the desired carboxylic acid had >98 area % of all peaks. The pooled $CCl_4$ extracts of the carbonylation reactions, taken up in water, from autoclaves A1 to A8 were washed with water, the organic solvent was removed under reduced pressure and the residue was dried under high vacuum. 250 mg (0.93 mmol, 64% of theory) of crystalline solid were obtained, whose $^1$H NMR spectrum, HPLC retention and UV spectrum were identical to those of the authentic reference substance. $^1$H NMR ($CDCl_3$): δ=1.63 (s, 6H, 2×$CH_3$), 2.23 (qui, 2H, $CH_2$), 3.16 (t, 2H, $CH_2$), 3.67 (t, 2H, $CH_2$), 7.50 (~d, 2H, arom. H), 7.96 (~d, 2H, arom. H). UV (diode array spectrum): $\lambda_{max}$=261 and 207 nm.

Example 27

Synthesis of 1-[4-(1-hydroxy-1-methylethyl)phenyl] 4-chlorobutan-1-one (Formula X, Y=Cl) by Benzylic Oxidation of (III) ($R^1=R^2$=methyl, $R^3$=4-chlorobutyryl) with Oxygen In a 100 ml three-neck round-bottom flask with mechanical stirrer [joints and stirrer shaft sealed with poly(monochlorotrifluoroethylene)], reflux condenser with an attached oxygen-filled balloon (natural latex) and an internal thermometer, 4.500 g (19.6 mmol) of 4-chloro-1-(4-isopropylphenyl)butan-1-one (97.9%, from reference example 2), 659 mg (3.92 mmol), 0.2 equivalent) of N-hydroxyphthalimide (NHP, 97%, Aldrich) and 99 mg (0.392 mmol, 0.02 equiv.) of cobalt (II) acetate tetrahydrate (99%, Merck) were dissolved in 25 ml of acetonitrile (Roth). The reaction mixture rapidly turned brown in the course of stirring under the closed oxygen atmosphere. The mixture was heated to 40° C. in an oil bath. After 7 hours, the solution turned green.

At this time, HPLC (system as in Examples 3-10) of a sample showed, in addition to NHP ($t_{ret}$ 3.9 min), 44 area % of the expected alcohol ($t_{ret}$ 11.0 min), 43 area % of the corresponding hydroperoxide ($t_{ret}$ 11.8 min), 4 area % of the reactant ($t_{ret}$=15.1 min) and 7 area % of a by-product ($t_{ret}$ 17.2 min). After stirring at 40° C. for a total of 9 hours, heating and stirring were switched off and the reaction mixture was left to stand at RT overnight. HPLC of a sample now showed, in addition to NHP, 59 area % of the alcohol, 32 area % of the hydroperoxide, 0.5 area % of reactant and 7 area % of the by-product. The solution was poured onto 3 times the amount of water and extracted with 3×30 ml of dichloromethane. The combined organic extracts were washed with 2×15 ml of water and concentrated under reduced pressure, and the oily residue was dried under high vacuum. It was chromatographed at medium pressure (flow rate 80 ml/min) through 434 g of silica gel 60 (Merck, 0.04-0.063 mm), in the course of which 100 mg (0.4 mmol) of the hydroperoxide, followed, after a few mixed fractions, by 2.98 g (12.38 mmol, 63% of theory) of the desired alcohol were eluted, development being effected first using 1.8 l of 90:10 n-heptane/ethyl acetate and then using 1 l of 85:15 followed by 1 l of 80:20. Spectra and physical properties of the alcohol were identical to those of the product from Example 28. The hydroperoxide had the following spectral data:

$^1$H NMR ($CDCl_3$); δ=1.62 (s, 2×$CH_3$, 6H), 2.22 (t, 2H, $CH_2$), 3.17 (t, 2H, $CH_2$), 3.67 (t, 2H, $CH_2$), 7.57 (~d, 2H, arom. H), 7.75 (br s, 1H, OOH), 7.97 (~d, 2H, arom. H). $^{13}$C NMR (CDCl$_3$); δ=26.10 (2×CH$_3$), 26.78 (CH$_2$), 35.33 ($\underline{C}$H$_2$—CO), 44.65 (CH$_2$Cl), 83.79 (C—OOH), 125.74 (2× arom. CH), 128.32 (2× arom. CH), 135.76 (arom. C), 140.27 (arom. C), 150.55 (C=O). IR (liquid film): v=3600-3200 (br, OO—H), 1673 (C=O), 1266, 1227, 907, 730 cm$^{-1}$. MS (ESI+): m/z=259.12 (M+H$^+$ with $^{37}$Cl), 257.10 (M+H$^+$ with $^{35}$Cl).

Example 28

Synthesis of 1-[4-(1-hydroxy-1-methylethyl)phenyl]-4-chlorobutan-1-one (Formula X; Y=Cl) by hydrolysis of the bromide (formula VIII, Y=Cl) in pH7 buffer A pH7 buffer solution was prepared by dissolving 2.02 g (20 mmol) of triethylamine in 1 l of Millipore water and then adding glacial acetic acid up to pH 7.00.

In a 2 l round-bottom flask, 19.1 g (61.4 mmol) of 1-[4-(1-bromo-1-methyl-ethyl)phenyl]-4-chlorobutan-1-one (formula VIII, Y=Cl) (97.5%, Example 1) were dissolved under nitrogen in 765 ml of acetonitrile, then 383 ml of the buffer solution were added. The solution was left to stand in the closed flask at RT for 1 day and at +3° C. in a refrigerator for 2 days. It was then concentrated under reduced pressure to a third of the original volume and extracted with 1×100 and 2×50 ml of dichloromethane. The combined extracts were washed with 50 ml of water and the aqueous phase was back-extracted with 50 ml of dichloromethane. The combined dichloromethane phases were concentrated under reduced pressure and the remaining oil was dried under high vacuum. The mixture, dissolved in 30 ml of 8:2 n-heptane/ethyl acetate plus 2 ml of dichloromethane, was introduced into a medium-pressure chromatography column (diameter 9.5 cm, length 48 cm) which contained 1.9 kg of silica gel 60 (Merck, 0.04-0.063 mm) which had been conditioned beforehand with 6 l of 9:1 heptane/ethyl acetate. Development and elution were effected at a flow rate of 160 ml/min with a heptane/ethyl acetate gradient (2 l 90:10, 6 l 80:20, 5 l 75:25, 3 l 70:30, 1 l 60:40, 3 l 55:45, 5 l 50:50). Fractions of 150 ml were collected. The pure product eluted in fractions 54-75. The solvents were removed under reduced pressure and the residue dried with stirring under high vacuum. Yield: 11.1 g (46.1 mmol, 75% of theory) of an oil.

According to HPLC (system as in Examples 3-10), the alcohol had a purity of 99.2 area % (t$_{ret}$ 10.9 min). GC (system as in reference example 2): t$_{ret}$ 12.0 min. Even in the pure state, the alcohol is a slightly cloudy, colorless oil which crystallizes in a freezer cabinet but melts again close to room temperature in the course of heating. It is stored under argon in a freezer cabinet. In the course of storage at room temperature, it turns yellow after a few days. $^1$H NMR (CDCl$_3$:

δ=1.60 (s, 6H, 2×CH$_3$), 2.03 (br s, 1H, OH), 2.22 (qui, 2H, CH$_2$), 3.17 (t, 2H, CH$_2$), 3.67 (t, 2H, CH$_2$), 7.59 (~d, 2 H, arom. H), 7.94 (~d, 2H, arom. H). $^{13}$C NMR (CDCl$_3$): d=26.81 (CH$_2$), 31.68 (2×CH$_3$), 35.29 ($\underline{C}$H$_2$—CO), 44.67 (CH$_2$—Cl), 72.54 (C—OH), 124.76 (2× arom. CH), 128.12 (2× arom. CH), 135.21 (arom. C), 154.62 (arom. $\underline{C}$—CO), 198.69 (C=O)

Examples 29-36

Synthesis of 2-[4-(4-chlorobutyryl)phenyl]-2-methylpropionic acid (Formula I, R$^1$=R$^2$=methyl; R$^3$=4-chlorobutyryl) by Carbonylation of the Alcohol (Formula X, Y=Cl) in Superacid at 30° C. in the Presence of Preformed Copper(I) Tricarbonyl Ion as an Additive 3.0 mg (0.0419 mmol, 20.1 mol % based on the reactant) of Cu$_2$O were weighed into each of the eight miniautoclaves (A1 to A8). The mini-autoclaves were installed into the reactor block and sealed. The autoclaves were purged and charged in an argon countercurrent, by means of inertized GC vials, with in each case 0.5 ml of 98% trifluoromethanesulfonic acid CF$_3$SO$_3$H (Aldrich). The miniautoclaves were each sealed with a gas-tight septum and purged again, and the carbon monoxide reaction gas was injected up to the desired pressure (5 bar for A1 and A2, 25 bar for A3 and A4, 40 bar for A5 and A6, 60 bar for A7 and A8). The reaction block was heated to the reaction temperature of 30° C. with magnetic stirring of the miniautoclaves (200 revolutions/min). In the 30-minute preformation phase which followed, reaction of the Cu$_2$O with CO formed the [Cu(CO)$_3$]+ additive in situ. In this period, the reactant solution was prepared. To this end, 1.00 g (4.15 mmol) of 1-[4-(1-hydroxy-1-methylethyl)phenyl]-4-chloro-butan-1-one (from Example 28) was weighed into a 2.5 ml standard flask and made up to the mark with about 1.5 ml of carbon tetrachloride to form a clear solution. After the preformation phase had ended, in each case 125 µl (0.208 mmol) of the reactant solution were syringed by means of a pressure-tight glass syringe through the septum into each of the eight miniautoclaves manually within 1 minute in each case. After the reactant had been added, the reaction time of 4.0 hours commenced. Only at the start of the reaction was the CO gas injected precisely up to the intended pressure. In the course of the carbonylation, the internal autoclave pressure falls off somewhat as a result of CO consumption. The experiment is thus not isobaric. After the reaction time had ended, the reactor block was cooled to 25° C. and decompressed. Workup and analysis were effected as described for Examples 3-10. Reaction parameters and calculated yields are compiled in the table:

| Autoclave No. | Reactant [mmol] | Additive [mmol] | Acid 0.5 ml | CO pressure [bar] | Temp. [° C.] | Yield (I) [% of theory] |
|---|---|---|---|---|---|---|
| A1 | alcohol 0.208 | Cu$_2$O 0.0419 | CF$_3$SO$_3$H | 5 | 30 | 53 |
| A2 | alcohol 0.208 | Cu$_2$O 0.0419 | CF$_3$SO$_3$H | 5 | 30 | 54 |
| A3 | alcohol 0.208 | Cu$_2$O 0.0419 | CF$_3$SO$_3$H | 25 | 30 | 58 |
| A4 | alcohol 0.208 | Cu$_2$O 0.0419 | CF$_3$SO$_3$H | 25 | 30 | 56 |
| A5 | alcohol 0.208 | Cu$_2$O 0.0419 | CF$_3$SO$_3$H | 40 | 30 | 59 |
| A6 | alcohol 0.208 | Cu$_2$O 0.0419 | CF$_3$SO$_3$H | 40 | 30 | 54 |
| A7 | alcohol 0.208 | Cu$_2$O 0.0419 | CF$_3$SO$_3$H | 60 | 30 | 58 |
| A8 | alcohol 0.208 | Cu$_2$O 0.0419 | CF$_3$SO$_3$H | 60 | 30 | 52 |

Examples 37-44

Synthesis of 2-[4-(4-chlorobutyryl)phenyl]-2-methylpropionic acid (Formula I, $R^1=R^2$=methyl; $R^3$=4-chlorobutyryl) by Carbonylation of the Alcohol (Formula X; Y=Cl) in Superacid at 40° C. in the Absence of Additive The carbonylations were carried out as in Examples 29-36, but at 40° C. and in the absence of additive. The results are summarized in the table:

| Autoclave No. | Reactant [mmol] | Additive [mmol] | Acid 0.5 ml | CO pressure [bar] | Temp. [° C.] | Yield (I) [% of theory] |
|---|---|---|---|---|---|---|
| A1 | alcohol 0.208 | — | CF$_3$SO$_3$H | 5 | 40 | 43 |
| A2 | alcohol 0.208 | — | CF$_3$SO$_3$H | 5 | 40 | 47 |
| A3 | alcohol 0.208 | — | CF$_3$SO$_3$H | 25 | 40 | 51 |
| A4 | alcohol 0.208 | — | CF$_3$SO$_3$H | 25 | 40 | 52 |
| A5 | alcohol 0.208 | — | CF$_3$SO$_3$H | 40 | 40 | 53 |
| A6 | alcohol 0.208 | — | CF$_3$SO$_3$H | 40 | 40 | 53 |
| A7 | alcohol 0.208 | — | CF$_3$SO$_3$H | 60 | 60 | 51 |
| A8 | alcohol 0.208 | — | CF$_3$SO$_3$H | 60 | 60 | 50 |

Examples 45-52

Synthesis of 2-[4-(4-chlorobutyryl)phenyl]-2-methylpropionic acid (Formula I, $R^1=R^2$=methyl; $R^3$=4-chlorobutyryl) by Carbonylation of the Alcohol (Formula X, Y=Cl) in Superacid or in Conc. Sulfuric Acid at 40° C. Under 87 Bar of CO Pressure In each case 3.0 mg (0.0419 mmol, 20.1 mol % based on the reactant) of Cu$_2$O were weighed into the miniautoclaves A3, A4, A7 and A8; the mini-autoclaves A1, A2, A5 and A6 were left without additive. The eight mini-autoclaves were installed into the reactor block and sealed. The autoclaves were purged, cooled to 0° C. and charged in an argon countercurrent, by means of inertized GC vials, with 0.5 ml of the particular solvent (96% sulfuric acid for A1-A4, 98% trifluoromethanesulfonic acid CF$_3$SO$_3$H for A5-A8) and with 125 µl (0.208 mmol) of the reactant solution (in CCl$_4$). The preformation of the Cu$_2$O-containing mixtures was dispensed with in these reactions owing to the rigid, automated reaction sequence. The miniautoclaves were sealed and purged again, and 87 bar of the carbon monoxide reaction gas were injected.

The reaction block was heated to 40° C. with magnetic stirring of the miniautoclaves (200 revolutions/min). The heating time was 15 minutes. The mixture was then stirred at 40° C. for 4 hours. In the course of the carbonylation, the internal autoclave pressure falls off somewhat as a result of CO consumption. The experiment is thus not isobaric. After the reaction time had ended, the reactor block was cooled to 25° C. and decompressed. Workup and analysis were effected as described for Examples 3-10. Reaction parameters and calculated yields are compiled in the table:

| Autoclave No. | Reactant [mmol] | Additive [mmol] | Acid 0.5 ml | CO pressure [bar] | Temp. [° C.] | Yield (I) [% of theory] |
|---|---|---|---|---|---|---|
| A1 | alcohol 0.208 | — | H$_2$SO$_4$ | 87 | 40 | 0 |
| A2 | alcohol 0.208 | — | H$_2$SO$_4$ | 87 | 40 | 0 |
| A3 | alcohol 0.208 | Cu$_2$O 0.0419 | H$_2$SO$_4$ | 87 | 40 | 0 |
| A4 | alcohol 0.208 | Cu$_2$O 0.0419 | H$_2$SO$_4$ | 87 | 40 | 0 |
| A5 | alcohol 0.208 | — | CF$_3$SO$_3$H | 87 | 40 | 53 |
| A6 | alcohol 0.208 | — | CF$_3$SO$_3$H | 87 | 40 | 52 |
| A7 | alcohol 0.208 | Cu$_2$O 0.0419 | CF$_3$SO$_3$H | 87 | 40 | 53 |
| A8 | alcohol 0.208 | Cu$_2$O 0.0419 | CF$_3$SO$_3$H | 87 | 40 | 51 |

Example 53

Isolation of the 2-[4-(4-chlorobutyryl)phenyl]-2-methylpropionic Acid Product (Formula I, $R^1=R^2=$methyl; $R^3=$4-chlorobutyryl) from the Carbonylations of Examples 29-52

The pooled 0014 extracts of the carbonylation reactions from Examples 29-44 and 49-52 taken up in water were washed with water, the organic solvent was removed under reduced pressure and the residue was dried under high vacuum. 622 mg (2.31 mmol, 56% of theory) of crystalline solid were obtained, whose $^1$H NMR spectrum, HPLC retention and UV spectrum were identical to those of the authentic reference substance.

Example 54

Synthesis of the alkene 1-[4-(2-propenyl)phenyl]-4-chlorobutan-1-one [Formula II, $R^1=$methyl, $R^3=$4-chlorobutyryl, $R^4=$methylene] by Dehydrobromination of the Benzylic Bromide 20.6 g (67.8 mmol) of 1-[4-[1-bromo-1-methylethyl]phenyl]-4-chlorobutan-1-one [formula VIII, Y=Cl] (97.5%, Example 1) were added to a mixture of 14.8 g (170 mmol) of lithium bromide and 7.6 g (102 mmol) of lithium carbonate in 60 ml of DMF and stirred at RT for 1 day. Water was added to the suspension until a clear solution had formed. This was extracted with 4×50 ml of n-heptane and the combined heptane extracts were washed with 3×50 ml of water. The heptane phase was concentrated under reduced pressure and the residue dried under high vacuum (16.6 g of crude product). Medium pressure chromatography by 900 g of silica gel 60 (Merck, 0.04-0.063 mm) with an n-heptane/diethyl ether gradient (99:1 to 90:10) gave 10.7 g (48.0 mmol, 71% of theory) of colorless, flaky crystals, m.p. 54-55° C. $^1$H NMR (CDCl$_3$: δ=2.19 (s, 3H, CH$_3$), 2.22 (qui, 2H, CH$_2$), 3.18 (t, 2H, CH$_2$), 3.69 (t, 2H, CH$_2$), 5.21 (s, 1H, =CH), 5.48 (s, 1H, =CH), 7.55 (~d, 2H, arom. H), 7.94 (~d, 2H, arom. H).

Examples 55-70

Synthesis of 2-[4-(4-chlorobutyryl)phenyl]-2-methylpropionic acid (Formula I, $R^1=R^2=$methyl; $R^3=$4-chlorobutyryl) by Carbonylation of the Bromide (VIII, Y=Cl) in Trifluoromethanesulfonic Acid in the Presence of Added, Defined Amounts of Water The miniautoclaves, vessels, HPLC bottles and syringes used were dried in a drying cabinet at 60° C. under reduced pressure. 8 HPLC bottles were charged in a glovebox with in each case 75 mg of the bromide (VIII, Y=Cl; 98.5%) dissolved in 150 μl in each case of 0014. In eight glass vessels, water was added to trifluoromethanesulfonic acid from Central Glass (purity >99.5% by weight, water content 160 ppm, corresponding to a water content of 4 mol % based on reactant VIII (Y=Cl)) in exactly such an amount that it subsequently had water contents of 4 mol %, 23 mol %, 45 mol %, 90 mol %, 100 mol %, 200 mol %, 500 mol % and 2000 mol % respectively based on the reactant VIII (Y=Cl). The corresponding percentages by weight of water can be taken from the table which follows. In a glovebox, in each case 500 μl of this aqueous acid was transferred under argon to eight HPLC vials by means of in syringe.

The rack with the eight 2 ml miniautoclaves (A1 to A8) was inertized with argon and the acid from the eight HPLC vials was forced with argon and against an argon current over into the eight miniautoclaves. At −5° C., the miniautoclaves were purged, then CO was injected and the reaction temperature of 0° C. was established. The pressure was adjusted to 40 bar. The CCl$_4$ solutions of the bromide were syringed in by means of a gas-tight syringe (addition time about 30 seconds for each solution) and then allowed to react for 20 hours. 8 test tubes were charged with 5 ml each of CCl$_4$. The miniautoclaves were decompressed and opened. The contents of each of the miniautoclaves was poured by means of a funnel into one of the test tubes each. In each case 2 ml of ice-water were introduced additionally and then autoclave and funnel were rinsed in each case with 10 ml of CCl$_4$. The phases were agitated and allowed to separate. In each case 0.5 ml of the organic phase was then removed and concentrated by evaporation in a nitrogen stream. The residue was in each case taken up in 2.5 ml of acetonitrile and analyzed at a dilution of 1:30 in HPLC. The yield was calculated from the peak area of the carboxylic acid using a calibration curve.

| Autoclave No. | Reactant [mmol] | Acid 0.5 ml % by wt. of H$_2$O | total water content [based on reactant] | CO pressure [bar] | Temp. [° C.] | Yield (I) [% of theory] |
|---|---|---|---|---|---|---|
| A1 | bromide 0.243 | CF$_3$SO$_3$H 0.02% H$_2$O | 4 mol % | 40 | 0 | 16 |
| A2 | bromide 0.243 | CF$_3$SO$_3$H 0.118% H$_2$O | 23 mol % | 40 | 0 | 50 |
| A3 | bromide 0.243 | CF$_3$SO$_3$H 0.235% H$_2$O | 45 mol % | 40 | 0 | 74 |
| A4 | bromide 0.243 | CF$_3$SO$_3$H 0.471% H$_2$O | 90 mol % | 40 | 0 | 93 |
| A5 | bromide 0.243 | CF$_3$SO$_3$H 0.522% H$_2$O | 100 mol % | 40 | 0 | 95 |
| A6 | bromide 0.243 | CF$_3$SO$_3$H 1.044% H$_2$O | 200 mol % | 40 | 0 | 99 |
| A7 | bromide 0.243 | CF$_3$SO$_3$H 2.610% H$_2$O | 500 mol % | 40 | 0 | 87 |
| A8 | bromide 0.243 | CF$_3$SO$_3$H 10.44% H$_2$O | 2000 mol % | 40 | 0 | 0 |

A further rack of 8 miniautoclaves was used to carry out an identical experiment with the sole difference that the carbonylations were terminated as early as after 5 hours instead of after 20 hours. The results are compiled in the table which follows. Owing to a fault, the yields in the autoclaves A5, A7 and A8 could not be determined here.

| Autoclave No. | Reactant [mmol] | Acid 0.5 ml % by wt. of $H_2O$ | total water content [based on reactant] | CO pressure [bar] | Temp. [°C.] | Yield (I) [% of theory] |
|---|---|---|---|---|---|---|
| A1 | bromide 0.243 | $CF_3SO_3H$ 0.02% $H_2O$ | 4 mol % | 40 | 0 | 19 |
| A2 | bromide 0.243 | $CF_3SO_3H$ 0.118% $H_2O$ | 23 mol % | 40 | 0 | 45 |
| A3 | bromide 0.243 | $CF_3SO_3H$ 0.235% $H_2O$ | 45 mol % | 40 | 0 | 67 |
| A4 | bromide 0.243 | $CF_3SO_3H$ 0.471% $H_2O$ | 90 mol % | 40 | 0 | 91 |
| A5 | bromide 0.243 | $CF_3SO_3H$ 0.522% $H_2O$ | 100 mol % | 40 | 0 | not determined |
| A6 | bromide 0.243 | $CF_3SO_3H$ 1.044% $H_2O$ | 200 mol % | 40 | 0 | 94 |
| A7 | bromide 0.243 | $CF_3SO_3H$ 2.610% $H_2O$ | 500 mol % | 40 | 0 | not determined |
| A8 | bromide 0.243 | $CF_3SO_3H$ 10.44% $H_2O$ | 2000 mol % | 40 | 0 | not determined |

In the carbonylation of the bromide of the formula (VIII) (Y=Cl) in trifluoromethanesulfonic acid, the completeness of the conversion of the reactant (VIII) and the yield and purity of the desired carboxylic acid (I) achieved depends to a high degree upon the water content of the trifluoromethanesulfonic acid.

When dry trifluoromethanesulfonic acid [water content 160 ppm, corresponding to a water content of 4 mol % based on the reactant (VIII)] was used for the carbonylation (0° C., 40 bar of CO) without further addition of water, this gave rise to a conversion of less than 50% of the reactant (II). The carboxylic acid (I) was formed with a yield of from 16% to 19% and the HPLC analysis of the unpurified carbonylation solution indicated an unclean reaction. Under otherwise identical reaction parameters, it was possible with increasing water content of the trifluoromethanesulfonic acid to continuously increase the conversion and the yield of the carbonylation reaction and a clean reaction was obtained. The following table once again summarizes the yield as a function of the amount of water:

|  |  | mol % of water, based on reactant (VIII) used, in trifluoromethanesulfonic acid ||||||||
|---|---|---|---|---|---|---|---|---|---|
|  |  | 4 | 23 | 45 | 90 | 100 | 200 | 500 | 2000 |
| Yield (% of theory) of carboxylic acid (I), based on reactant (II) used | 20 h | 16 | 50 | 74 | 93 | 95 | 99 | 87 | 0 |
|  | 5 h | 19 | 45 | 67 | 91 |  | 94 |  |  | h means hours

In the presence of 100-200 mol % of water, up to 99% conversion of the reactant (VIII), a very clean reaction and up to 99% yield of the carboxylic acid (I) were obtained. While the yield fell only to 87% in the presence of 500 mol % of water, distinctly higher water contents once again brought about complete failure of the carbonylation reaction. At a water content of 2000 mol %, which corresponds approximately to the use of trifluoromethanesulfonic acid monohydrate, no carboxylic acid (I) was formed.

Example 71

Synthesis of 2-[4-(4-chlorobutyryl)phenyl]-2-methylpropionic acid (Formula I, $R^1=R^2$=methyl; $R^3$=4-chlorobutyryl) by Preparative Carbonylation of the Bromide (VIII, Y=Cl) in Trifluoromethanesulfonic Acid in the Presence of 200 mol % of Water Based on Reactant Metering of the reactant in concentrated CCl4 solution; workup of the carbonylation reaction with aqueous sodium carbonate solution.

A 500 ml Hasteloy Büchi autoclave with sparging stirrer was charged with 100 ml of trifluoromethanesulfonic acid (from Central Glass Co., 99.5%, 0.02% water) to which 1.72 ml of water had been added beforehand. The water content of the acid was thus 200 mol % based on the reactant [bromide of the formula (VIII)]. The autoclave was closed in a gas-tight manner, nitrogen was injected and decompressed, then, three times each, CO was injected, the mixture was stirred vigorously and the autoclave was decompressed again. CO was then injected to 40 bar, the stirrer was adjusted to a rotation rate of 1000 revolutions/min and the reaction temperature was adjusted to 0° C. By means of an HPLC pump, a solution of 15.7 g of 94.9% 1-[4-(1-bromo-1-methylethyl)phenyl]-4-chlorobutan-1-one (49.07 mmol) in 19.0 ml of carbon tetrachloride were metered in at 0° C. within 3 minutes and then the mixture was stirred under 40 bar of CO at 0° C. for a further 22 hours. The autoclave was decompressed and the contents (150 ml of a yellow, clear solution on whose surface a $CCl_4$ phase was disposed) were discharged. The autoclave was rinsed with 150 ml of $CCl_4$ with stirring and this rinsed solution was discarded.

The trifluoromethanesulfonic acid solution was added dropwise to 400 g of ice with stirring within 15 minutes, in the course of which the reaction solution became decolorized, the temperature fell to below 0° C. and a colorless solid precipitated out. 50 ml of dichloromethane were added with stirring. The lower organic, pale yellow phase was separated from the upper aqueous, colorless phase (pH 0.1). The aqueous phase was extracted with a further 50 ml of dichloromethane. The combined organic phases (177.37 g) were washed twice with 50 ml each time of ice-water for 1 minute each (last wash solution had pH 3.7). The organic phase was extracted at 0° C. with 50 ml, and then once more with 25 ml, of ice-cold 1M aqueous sodium carbonate solution. The last aqueous extract had pH 10.5. The combined aqueous extracts (pH 9.4) were freed of residual dichloro-methane by bubbling nitrogen through and then acidified at from 0 to +5° C. (ice-cooling) with 18 ml of 30% hydrochloric acid with stirring, in the course of which the carboxylic acid precipitated out in crystalline form. The pH persisted for a prolonged period at pH 6.7 to 6.5. The mixture was stirred in an ice bath for 0.5 hour. The precipitate was filtered off with suction, washed with 50 ml of ice-water and dried in a desiccator over phosphorus pentoxide under high vacuum at room temperature overnight. 12.7 g of colorless crystals (47.26 mmol, 96.3 of theory) were obtained. HPLC analysis of the carboxylic acid gave a purity of 99.4 area %.

Example 72

Synthesis of 2-[4-(4-chlorobutyryl)phenyl]-2-methylpropionic acid (Formula I, $R^1=R^2$=methyl; $R^3$=4-chlorobutyryl) by Preparative Carbonylation of the Bromide (VIII, Y=Cl) in Trifluoromethanesulfonic Acid in the Presence of 200 mol % of Water Based on Reactant Metering of the reactant in $CH_2Cl_2$ solution; workup of the carbonylation reaction with aqueous sodium carbonate solution.

A 500 ml Hasteloy Büchi autoclave with sparging stirrer was charged with 100 ml of trifluoromethanesulfonic acid (from Central Glass Co., 99.5%, 0.02% water) to which 1.72 ml of water had been added beforehand. The water content of the acid was thus 200 mol % based on the reactant [bromide of the formula (VIII)]. The autoclave was closed in a gas-tight manner, nitrogen was injected and decompressed, then, three times each, CO was injected, the mixture was stirred vigorously and the autoclave was decompressed again. CO was then injected to 40 bar, the stirrer was adjusted to a rotation rate of 1000 revolutions/min and the reaction temperature was adjusted to 0° C. By means of an HPLC pump, a solution of 15.08 g of 94.9% 1-[4-(1-bromo-1-methylethyl)phenyl]-4-chlorobutan-1-one (47.13 mmol) in 19.0 ml of dichloromethane were metered in at 0° C. within 3 minutes and then the mixture was stirred under 40 bar of CO at 0° C. for a further 22 hours. The autoclave was decompressed and the contents (150 ml of a yellow, clear solution) were discharged. The autoclave was rinsed with 170 ml of dichloromethane with stirring and this rinsed solution was discarded.

The trifluoromethanesulfonic acid solution was worked up as in Example 71. 11.8 g of colorless crystals (43.91 mmol, 93.2% of theory) were obtained. HPLC analysis of the carboxylic acid gave a purity of 98.7 area %.

Example 73

Option of working up preparative carbonylation mixtures with sodium hydroxide solution instead of sodium carbonate solution. Stability of 2-[4-(4-chlorobutyryl)phenyl]-2-methylpropionic acid (formula I, $R^1=R^2$=methyl; $R^3$=4-chlorobutyryl) toward 1M sodium hydroxide solution under strict pH control at pH 10.

It is known that the chloroketo acid (formula I, $R^3$=4-chlorobutyryl) is converted readily even under weakly basic conditions to the cyclopropyl-keto acid (formula I, $R^3$=cyclopropyl). It was investigated whether the chloroketo acid can be extracted into 1 M sodium hydroxide solution under strict pH control at pH 10 without ring closure, so that a workup of the carbonylation solution with 1M sodium hydroxide solution instead of sodium carbonate solution is possible.

2.71 g (10 mmol) of 2-[4-(4-chlorobutyryl)phenyl]-2-methylpropionic acid (HPLC purity 99.4 area %, product from Example 71) were dissolved in 24 ml of dichloromethane. 1 ml of water was added and the mixture was then adjusted in an ice bath at internal temperature from 0 to +5° C. exactly to pH 10.0 with 10.3 ml of 1 M sodium hydroxide solution, initially by hand, later by syringe pump, within 25 minutes. The pH persisted for a long period at 7.65 and rose very rapidly after addition of one equivalent of sodium hydroxide solution (10.0 ml). In this last phase of the titration, the sodium hydroxide solution had to be added dropwise in order to prevent pH 10.0 from being overshot. The organic phase was removed. The aqueous phase was freed of residual dichloromethane by bubbling nitrogen through, then acidified to pH 1 with 2 ml of 30% hydrochloric acid solution at from 0 to +5° C. with ice cooling. The suspension was stirred in an ice bath for a further 30 minutes, and the solid was filtered off with suction, washed with 5 ml of ice-water and dried over phosphorus pentoxide under high vacuum. 2.60 g (9.67 mmol, 96.7% of theory) of colorless crystals were obtained, which had a purity of 99.0 area % by HPLC analysis. The cyclopropylketo acid impurity was present only to an extent of 0.3 area %, the hydroxyketo acid (formula I, R3=4-hydroxybutyryl) impurity only to an extent of 0.2 area %.

Workup of carbonylation solutions with 1M sodium hydroxide solution is thus possible.

Examples 74-81

Synthesis of 2-[4-(4-chlorobutyryl)phenyl]-2-methylpropionic acid (Formula I, $R^1=R^2$=methyl; $R^3$=4-chlorobutyryl) by Carbonylation of the Bromide (VIII, Y=Cl) in Alternative Superacids The experimental procedure was analogous to Examples 55-70. The reaction time was 4 hours. Aluminum trichloride was transferred as a solid into the reactors A7 and A8, then the dichloromethane was added, and subsequently additionally 4.5 µl of water into reactor A8. The commercial boron trifluoride-phosphoric acid complex (CAS No.: 13669-76-6) used in the reactors A5 and A6 had b.p. 147° C. and d=1.840. 4.5 µl of water were additionally added to reactor A6.

| Autoclave No. | Reactant [mmol] | Acid 0.5 ml | total water content [based on reactant] | CO pressure [bar] | Temp. [° C.] | Yield (I) [% of theory] |
|---|---|---|---|---|---|---|
| A1 | bromide 0.206 | $CF_3SO_3H$ 98% | about 50 mol % | 40 | 0 | 67 |
| A2 | bromide 0.206 | $FSO_3H$ 98% | unknown | 40 | 0 | 36 |

-continued

| Autoclave No. | Reactant [mmol] | Acid 0.5 ml | total water content [based on reactant] | CO pressure [bar] | Temp. [° C.] | Yield (I) [% of theory] |
|---|---|---|---|---|---|---|
| A3 | bromide 0.206 | $CH_3SO_3H$ | unknown | 40 | 0 | 1 |
| A4 | bromide 0.237 | 40% $CH_3SO_3H$ 60% $CF_3SO_3H$ | unknown | 40 | 0 | 16 |
| A5 | bromide 0.206 | $BF_3 \cdot H_3PO_4$ | unknown | 40 | 0 | 5 |
| A6 | bromide 0.243 | $BF_3 \cdot H_3PO_4$ | 100 mol % | 40 | 0 | 17 |
| A7 | bromide 0.206 | 10% $AlCl_3$ in $CH_2Cl_2$ | unknown | 40 | 0 | 0 |
| A8 | bromide 0.243 | 10% $AlCl_3$ in $CH_2Cl_2$ | 100 mol % | 40 | 0 | 3 |

Example 82

Synthesis of cyclopropyl(4-isopropylphenyl)methanone (Formula III, $R^1=R^4$=methyl, $R^3$=cyclopropylcarbonyl)

In a 4 l four-neck round-bottom flask with glass stirrer shaft, PTFE stirrer blade, Pt 100 thermometer and pH electrode, 457.9 g (2.037 mol) of 4-chloro-1-(4-isopropylphenyl)butan-1-one (formula III, $R^1=R^2$=methyl, $R^3$=4-chlorobutyryl) were dissolved in 1832 g of methanol at 40° C. with stirring (pH 0.7). 250 ml of water were added (pH 2.17) and the pH was adjusted to 12.6 with 32% aqueous sodium hydroxide solution. During the reaction time of 2.5 hours, the falling pH was constantly adjusted back to pH 12.5 with sodium hydroxide solution. The total consumption of sodium hydroxide solution was 272.0 g. In order to dissolve the sodium chloride which formed, 200 ml of water were added in portions during the reaction. The reflux condenser was replaced by a short Claisen condenser, and then methanol/water was distilled off under reduced pressure (approx. 60 mbar) at 30° C. During distillation, solid began to precipitate out. In order to keep the suspension stirrable, another 450 ml of water were added. Once the mass of the distillate was 980 g, the solid was filtered off with suction (moist 352 g, dry 325 g), the mother liquor was cooled to +2° C. and, after 30 minutes, the solid which has precipitated out once again was likewise filtered off with suction (moist 35 g, dry 33 g). The mass of the mother liquor thereafter was 827 g. Overall yield: 358 g (1.902 mol, 93.3% of theory). The purity of this crude product was >99.7 area % according to 100% analysis in GC and HPLC. In the $^1H$ and $^{13}C$ NMR, no impurities were visible. The product did, though, still contain minor inorganic constituents and had a water content of 0.89% by weight (Karl-Fischer titration) which, under reduced pressure over phosphorus pentoxide, could not be reduced to the water content of <0.1% desired for the subsequent reaction within a sensible period. 212.7 g of the crude product were dissolved to form a cloudy solution at 20° C. in 500 ml of n-heptane in a 1 l Erlenmeyer flask, in the course of which the cooling which occurred was balanced out with a warm water bath. The solution was filtered through a clarifying layer and washed with n-heptane. The clear colorless filtrate was concentrated under reduced pressure. This gave a colorless oil which crystallized through almost entirely when it was cooled with dry ice under reduced pressure. The residual solvent was removed by drying under high vacuum. 207.3 g of colorless crystals (97.4% recovery wt./wt.), GC: 99.9 area %, water content (Karl-Fischer): 0.06%. $^1H$ NMR ($CDCl_3$): δ=1.02 (ddd, 2H, 2×CH), 1.22 (ddd, 2H, 2×CH), 1.27 (d, 6H, 2×$CH_3$), 2.66 (tt, 1H, CH), 2.97 (sept., 1H, CH), 7.32 (~d, 2H, arom. H), 7.96 (~d, 2H, arom. H). $^{13}C$ NMR ($CDCl_3$): δ=11.48 (2×$CH_2$), 17.09 (CH), 23.84 (2×$CH_3$), 34.36 (CH), 126.70 (2× arom. CH), 128.39 (2× arom. CH), 136.02 (arom. C), 154.31 (arom. H), 200.31 (C=O).

Example 83

Synthesis of [4-(1-chloro-1-methylethyl)phenyl]cyclopropylmethanone [formula II, X=Cl, $R^1=R^4$=methyl, $R^3$=cyclopropylcarbonyl] by Benzylic Chlorination with Tert-Butyl Hypochlorite with Illumination In a 1 l four-neck flask with mechanical stirrer, thermometer, reflux condenser with bubble counter and gas inlet tube for inert gas, 47.5 g (250 mmol) of cyclopropyl(4-isopropylphenyl)methanone (from Example 82) were dissolved in 475 ml of chlorobenzene (Merck Darmstadt), and the solution was bubbled through with nitrogen for 15 min in order to drive out dissolved oxygen. Subsequently, an ice-sodium chloride bath in a mirrored Dewar vessel was used to cool the mixture to −9° C. and then the inert gas feed was shut down. 43.5 ml (375 mmol, 1.5 equiv.) of tert-butyl hypochlorite were added and the nitrogen inlet tube was replaced by a stopper. Subsequently, irradiation was effected with an Osram Ultra Vitalux 300 W lamp ("sunlamp") with vigorous stirring. With maximum cooling, the reaction temperature rose within the first 5 minutes to the maximum value of 26° C., in the course of which the initially yellow solution became completely decolorized. Within the next 4 minutes, still under maximum cooling, the reaction temperature then fell back to +5° C. and was then, with gentle cooling, kept at 0-+1° C. for a further 6 minutes. The lamp was switched off. After a further 20 minutes in the cold bath, the colorless solution was concentrated in a good vacuum and the oily residue was dried under high vacuum with magnetic stirring. The product which had still not been dried completely stood overnight under protective gas in a refrigerator, in the course of which it crystallized. It was dried further under high vacuum to obtain 57.3 g of a partly crystalline, thick slurry. This was filtered with high suction through a glass frit under nitrogen blanketing. The crystals were washed twice with a little ice-cold n-heptane and suction-dried under nitrogen. 25.2 g of colorless coarse crystals were obtained, m.p. 37.5° C. After the solvent had been removed under reduced pressure and it had been left to stand overnight in a refrigerator, a further 12.4 g crystallized out of the mother liquor. Overall yield: 37.6 g (168.8 mmol, 67.5% of theory). The GC purity was 98.2 area %, the residual content of reactant 0.5 area %, the content of homobenzylic chloride 0.4 area % and the content of dichloride 0.9 area %. $^1H$ NMR ($CDCl_3$): δ=1.05 (ddd, 2H, 2×CH), 1.25 (ddd, 2H, 2×CH), 2.01 (s, 6H, 2×$CH_3$), 2.66 (tt, 1H, CH), 7.68 (~d, 2H, arom. H), 7.99 (~d, 2H, arom. H). $^{13}C$ NMR (CDCl$_3$): δ=11.77 (2×CH$_2$), 17.31 (CH), 34.25 (2×CH$_3$), 68.95 (C—Cl), 125.81 (2× arom. CH), 128.21 (2× arom. CH), 137.18 (arom. C), 150.92 (arom. C), 200.06 (C=O).

A similar photoreaction with 380 mg (2 mmol) of cyclopropyl(4-isopropyl-phenyl)methanone (from Example 82) in 3.8 ml of chlorobenzene with 0.35 ml (3 mmol) of tert-butyl hypochlorite gave the benzylic chloride without preceding purification by crystallization with a GC purity of 91 area % in 100% yield (wt./wt.).

A similar photoreaction with 380 mg (2 mmol) of cyclopropyl(4-isopropyl-phenyl)methanone (from Example 82) in 3.8 ml of benzotrifluoride (α,α,α-trifluorotoluene) with 0.35 ml (3 mmol) of tert-butyl hypochlorite gave the benzylic chloride without preceding purification by crystallization with a GC purity of 88 area % in 97% yield (wt./wt.).

Example 84

Synthesis of 1-[4-(1-chloro-1-methylethyl)phenyl]-4-chlorobutan-1-one (Formula IX, R$^1$=R$^4$=methyl) by Cyclopropyl Opening with Hydrogen Chloride In a 50 ml three-neck flask with magnetic stirrer bar, thermometer and reflux condenser, 23.7 g (105 mmol) of [4-(1-chloro-1-methyl-ethyl)phenyl]cyclopropylmethanone (from Example 83) were melted under nitrogen at 38° C. and bubbled through with nitrogen for 5 minutes, then heated to internal temperature 115° C. while still bubbling nitrogen through. At this temperature, hydrogen chloride gas from a lecture bottle was bubbled through slowly. Reaction monitoring by GC showed 6% residual reactant after 4 hours and 2% residual reactant after 7 hours. The reaction mixture was cooled in an ice bath while continuing to introduce HCl, then nitrogen was bubbled through in order to displace residual HCl. The weighing of the hydrogen chloride lecture bottle showed that a total of 53.2 g (1.47 mol) of HCl gas had been introduced. The reaction product was degassed under high vacuum, in the course of which the oil became significantly lighter in color. 26.9 g (103.8 mmol, 98.8% of theory wt./wt.) of yellow oil were obtained, which began to crystallize after several days in a freezer and finally crystallized through. GC analysis of the yellow oil showed a purity of 95.0 area %. The oil contained 1.7 area % of unconverted reactant and 3.3 area % of impurities. $^1$H NMR (CDCl$_3$): δ=2.00 (s, 6H, 2×CH$_3$), 2.23 (qui, 2H, CH$_2$), 3.18 (t, 2H, CH$_2$), 3.68 (t, 2H, CH$_2$), 7.68 (~d, 2H, arom. H), 7.96 (~d, 2H, arom. H).

Examples 85 and 86

Synthesis of 2-[4-(4-chlorobutyryl)phenyl]-2-methylpropionic acid (Formula I, R$^1$=R$^2$=methyl, R$^3$=4-chlorobutyryl) by Carbonylation of the Chloride (Formula IX, R$^1$=R$^4$=methyl) in Trifluoromethanesulfonic Acid with a Water Content of Approx. 50 Mol % Based on the Reactant The carbonylations were performed as a double batch in parallel in two 2 ml autoclaves, as described in Examples 23 and 24 for the corresponding bromide. In each case 0.206 mmol of the chloride (from Example 84) was allowed to react in 0.5 ml of 98% trifluoromethanesulfonic acid (water content approx. 50 mol % based on the reactant) under CO pressure 40 bar at 0° C. for 4 hours. By the external standard method (described in Example 3-10), HPLC analysis showed a yield of the desired carboxylic acid of 67% and 69% of theory. Yield and composition of the crude carbonylation solution were comparable to the result which had been achieved under the same reaction conditions with the bromide as the reactant (cf. Example 74).

Examples 87 and 88

Synthesis of 2-[4-(4-chlorobutyryl)phenyl]-2-methylpropionic acid (Formula I, R$^1$=R$^2$=methyl, R$^3$=4-chlorobutyryl) by Carbonylation of the Chloride (Formula IX, R$^1$=R$^4$=methyl) in Fluorosulfonic Acid The carbonylations were performed as a double batch in parallel in two 2 ml autoclaves, as described in Examples 23 and 24 for the corresponding bromide. In each case 0.206 mmol of the chloride (from Example 84) was allowed to react in 0.5 ml of 98% fluorosulfonic acid (water content not determined) under CO pressure 40 bar at 0° C. for 4 hours. By the external standard method (described in Example 3-10), HPLC analysis showed a yield of the desired carboxylic acid of 29% and 31% of theory. Yield and composition of the crude carbonylation solution were comparable to the result which had been achieved under the same reaction conditions with the bromide as the reactant (cf. Example 75).

Examples 89 and 90

Synthesis of 2-[4-(4-chlorobutyryl)phenyl]-2-methylpropionic acid (Formula I, R$^1$=R$^2$=methyl, R$^3$=4-chlorobutyryl) by Carbonylation of the Chloride (Formula IX, R$^1$=R$^4$=methyl) in Trifluoromethanesulfonic Acid with a Water Content of Approx. 200 Mol % Based on the Reactant The carbonylations were performed as a double batch in parallel in two 2 ml autoclaves, as described in Examples 23 and 24 for the corresponding bromide. In each case 0.206 mmol of the chloride (from Example 84) was allowed to react in 0.5 ml of 98% trifluoromethanesulfonic acid (water content approx. 200 mol % based on the reactant) under CO pressure 40 bar at 0° C. for 20 hours. By the external standard method (described in Example 3-10), HPLC analysis showed a yield of the desired carboxylic acid of 94% and 95% of theory. Yield and composition of the crude carbonylation solution were comparable to the result which had been achieved under the same reaction conditions with the bromide as the reactant (cf. Example 68).

We claim:
1. A process for preparing a compound of formula I

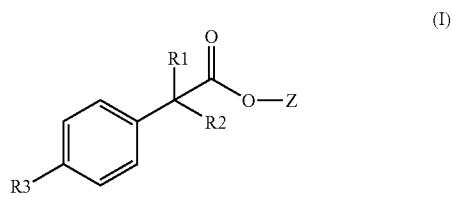

wherein:
R1 and R2 are each independently —(C$_1$-C$_4$)-alkyl;
R3 is —C(O)—(C$_1$-C$_4$)-alkyl, which is monosubstituted by Cl or Br, or —C(O)—(C$_3$-C$_6$)-cycloalkyl; and
Z is hydrogen or —(C$_1$-C$_{10}$)-alkyl;

comprising reacting a compound of formula II

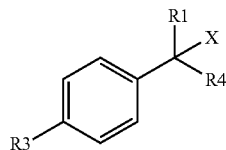

wherein:
R1 and R3 are each as defined in formula I;
X is Cl, Br or —OH; and
R4 is R2 or together with X form =CH$_2$ or =CH—($C_1$-$C_3$)-alkyl;
with carbon monoxide or a carbon monoxide-releasing compound in the presence of concentrated sulfuric acid, hydrogen fluoride or a superacid or mixtures thereof, and then
a) adding water to give the compound of formula I wherein Z is hydrogen, or
b) adding ($C_1$-$C_{10}$)-alkyl-OH when X is Cl or Br, or R4 together with X form =CH$_2$ or =CH—($C_1$-$C_3$)-alkyl, to give the compound of formula I wherein Z is —($C_1$-$C_{10}$)-alkyl, wherein the process is carried out in the presence of an additive which is converted rapidly under contact with carbon monoxide to metal carbonyls.

2. The process according to claim 1, wherein the additive is used in an amount of from 5 mol % to 100 mol % based on the compound of formula II.

3. A process for preparing a compound of formula I

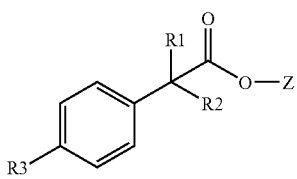

wherein:
R1 and R2 are each methyl;
R3 is 4-chlorobutyryl; and
Z is hydrogen or —($C_1$-$C_{10}$)-alkyl;
comprising reacting a compound of formula II

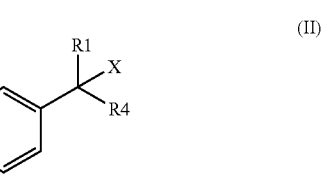

wherein:
R1 and R3 are each as defined in formula I;
X is Br; and
R4 is R2 or together with X form =CH$_2$ or =CH—($C_1$-$C_3$)-alkyl;
with carbon monoxide in the presence of trifluoromethanesulfonic acid and water, water being present in an amount of from 50 mol % to 500 mol % based on the compound of the formula II, and then
a) adding water to give the compound of formula I wherein Z is hydrogen, or
b) adding ($C_1$-$C_{10}$)-alkyl-OH when X is Cl or Br, or R4 together with X form =CH$_2$ or =CH—($C_1$-$C_3$)-alkyl, to give the compound of formula I wherein Z is —($C_1$-$C_{10}$)-alkyl.

4. The process according to claim 3, wherein water is used in an amount of from 90 mol % to 300 mol % based on the compound of formula II.

5. The process according to claim 3 wherein water is used in an amount of about 200 mol %, based on the compound of formula II.

* * * * *